(12) United States Patent
Bresler et al.

(10) Patent No.: US 8,101,736 B2
(45) Date of Patent: Jan. 24, 2012

(54) POLYNUCLEOTIDES AND POLYPEPTIDE OF HUMAN KV1.3, COMPOSITIONS COMPRISING SAME AND METHODS OF USING SAME

(75) Inventors: Tal Bresler, Haifa (IL); Yair Feld, Haifa (IL); Reem Miari, Sakhnin (IL); Lior Gepstein, Haifa (IL); Shimon Marom, Haifa (IL)

(73) Assignee: GeneGrafts Ltd., Haifa (IL)

( * ) Notice: Subject to any disclaimer, the term of this patent is extended or adjusted under 35 U.S.C. 154(b) by 786 days.

(21) Appl. No.: 12/084,654

(22) PCT Filed: Dec. 12, 2006

(86) PCT No.: PCT/IL2006/001431
§ 371 (c)(1),
(2), (4) Date: May 7, 2008

(87) PCT Pub. No.: WO2007/069247
PCT Pub. Date: Jun. 21, 2007

(65) Prior Publication Data
US 2010/0297083 A1 Nov. 25, 2010

Related U.S. Application Data

(60) Provisional application No. 60/750,342, filed on Dec. 15, 2005.

(51) Int. Cl.
*C07H 21/02* (2006.01)
*C07H 21/04* (2006.01)
(52) U.S. Cl. ...................................................... 536/23.1
(58) Field of Classification Search .................. None
See application file for complete search history.

(56) References Cited

U.S. PATENT DOCUMENTS
6,812,339 B1 * 11/2004 Venter et al. ............... 536/24.31

FOREIGN PATENT DOCUMENTS
| WO | WO 97/18332 | 5/1997 |
|----|----|----|
| WO | WO 03/035690 | 5/2003 |
| WO | WO 2007/069247 | 6/2007 |
| WO | WO 2008/078325 | 7/2008 |

OTHER PUBLICATIONS

International Search Report and the Written Opinion Dated Jul. 7, 2008 From the International Searching Authority Re.: Application No. PCT/IL06/01431.
Supplementary European Search Report and the European Search Opinion Dated Nov. 11, 2009 From the European Patent Office Re.: Application No. 06832233.8.
Douglass et al. "Characterization and Functional Expression of A Rat Genomic DNA Clone Encoding A Lymphocyte Potassium Channel", Journal of Immunology, XP002552292, 144(12): 4841-4850, Jun. 15, 1990. Abstract, Fig.3.
Kupper et al. "Intracellular and Extracellular Amino Acids That Influence C-Type Inactivation and Its Modulation in A Voltage-Dependent Potassium Channel", Pflügers Archiv: European Journal of Physiology, XP008112645, 430(1): 1-11, May 1, 1995. Abstract, Fig.5, Table 3, p. 2, r-h col. § 2, p. 9, § 1.
Shabtay et al. "Refractory Period Prolongation by Fibroblasts Overexpressing the Mutant Kv 1.3 H401W Channel in Computer Simulation and Pig Hearts", Molecular Therapy, XP002552291, 11: S360-S361, May 2005.
Somodi et al. "PH-Dependent Modulation of Kv1.3 Inactivation: Role of His399", American Journal of Physiology: Cell Physiology, XP002552293, 287(4): C1067-C1076, Oct. 2004. Abstract.
Visan et al. "Mapping of Maurotoxin Binding Sites on hKv1.2, hKv1.3, and h1KCa1 Channels", Molecular Pharmacology, XP002552294, 66(5): 1103-1112, Nov. 2004. Abstract, Fig.1.
Dreker et al. "Investigation of the Phenylalkylamine Binding Site in HKv1.3 (H399T), A Mutant With A Reduced C-Type Inactivated State", Molecular Pharmacology, 68(4): 966-973, 2005.
Panyi et al. "C-Type Inactivation of A Voltage-Gated K+ Channel Occurs by A Cooperative Mechanism", Biophysical Journal, 69: 896-903, 1995.
International Preliminary Report on Patentability Dated Jan. 22, 2009 From the International Bureau of WIPO Re.: Application No. PCT/IL2006/001431.
Communication Pursuant to Article 94(3) EPC Dated Jan. 27, 2010 From the European Patent Office Re.: Application No. 06832233.8.
Response Dated Jul. 27, 2010 to Communication Pursuant to Article 94(3) EPC of Jan. 27, 2010 From the European Patent Office Re.: Application No. 06832233.8.

* cited by examiner

*Primary Examiner* — Cherie M Woodward

(57) ABSTRACT

An isolated polypeptide comprising, contiguously, a first amino acid sequence being at least 90% homologous to amino acid coordinates 1-398 of SEQ ID NO: 2, a tryptophan residue and a second amino acid sequence being at least 90% homologous to amino acid coordinates 400-523 of SEQ ID NO:2. Also provided are polynucleotide sequences encoding this polypeptide and uses of same in the treatment of medical conditions associated with ion channel insufficiency.

1 Claim, 6 Drawing Sheets
(6 of 6 Drawing Sheet(s) Filed in Color)

SEQUENCE LISTING

```
<160> NUMBER OF SEQ ID NOS: 18

<210> SEQ ID NO 1
<211> LENGTH: 1572
<212> TYPE: DNA
<213> ORGANISM: Homo sapiens
<220> FEATURE:
<221> NAME/KEY: misc_feature
<223> OTHER INFORMATION: H399W mutant
```

```
<400> SEQUENCE: 1
atgaccgtgg tgcccgggga ccacctgctg gagccggagg tggccgatgg tggaggggcc    60
ccgcctcaag gcggctgtgg cggcggcggc tgcgaccgct acgagccgct gccgccctca   120
ctgccggccg cgggcgagca ggactgctgc ggggagcgcg tggtcatcaa catctccggg   180
ctgcgcttcg agacgcagct gaagaccctt tgccagttcc ccgagacgct gctgggcgac   240
cccaagcggc gcatgaggta cttcgacccg ctccgcaacg agtacttctt cgaccgcaac   300
cggcccagct tcgacgccat cctctactac tatcagtccg ggggccgcat ccgccggccg   360
gtcaacgtgc ccatcgacat tttctccgag gagatccgct tctaccagct gggcgaggag   420
gccatggaga gttccgcga ggacgagggc ttcctgcggg aggaggagcg gcccttgccc   480
cgccgcgact ccagcgcca ggtgtggctg ctcttcgagt accccgagag ctccggggccg   540 gcccggggca tcgccatcgt gtccgtgctg gtcatcctca tctccattgt catcttctgc   600
ctggagacgc tgccggagtt ccgcgacgag aaggactacc ccgcctcgac gtcgcaggac   660
tcattcgaag cagccggcaa cagcacgtcg gggtcccgcg caggagcctc cagcttctcc   720
gatcccttct tcgtggtgga gacgctgtgc atcatctggt tctccttcga actgctggtg   780
cggttcttcg cttgtcctag caaagccacc ttctcgcgaa acatcatgaa cctgatcgac   840
attgtggcca tcattcctta ttttatcact ctgggtaccg agctggccga acgacagggc   900
aatggacagc aggccatgtc tctggccatc ctgagggtca tccgcctggt aagggtcttc   960
cgcatcttca agctgtcgcg ccactccaag gggctgcaga tcctcgggca aacgctgaag  1020
gcgtccatgc gggagctggg attgctcatc ttcttcctct ttattggggt catcctttc   1080 tccagcgcg tctactttgc cgaggcagac gaccccactt caggtttcag cagcatcccg  1140
gatgccttct ggtgggcagt ggtaaccatg acaacagtgg gttacggcga tatgtggcca  1200
gtgaccatag ggggcaagat tgtgggatct ctctgtgcca tcgccggtgt cttgaccatc  1260
gcattgccag ttcccgtgat tgtttccaac ttcaattact tctaccaccg ggagacagaa  1320
ggggaagagc aatcccagta catgcacgtg gaagttgcc agcacctctc ctcttcagcc  1380
gaggagctcc gaaaagcaag gagtaactcg actctgagta agtcggagta tatggtgatc  1440
gaagaggggg gtatgaacca tagcgctttc ccccagaccc cttcaaaac gggcaattcc  1500 actgccacct gcaccacgaa caataatccc aactcttgtg tcaacatcaa aaagatattc  1560
accgatgttt aa                                                      1572
```

<210> SEQ ID NO 2
<211> LENGTH: 523
<212> TYPE: PRT
<213> ORGANISM: Homo sapiens

<400> SEQUENCE: 2

```
Met Thr Val Val Pro Gly Asp His Leu Leu Glu Pro Glu Val Ala Asp
  1               5                  10                  15

Gly Gly Gly Ala Pro Pro Gln Gly Gly Cys Gly Gly Gly Cys Asp
                 20                  25                  30

Arg Tyr Glu Pro Leu Pro Pro Ser Leu Pro Ala Ala Gly Glu Gln Asp
         35                  40                  45

Cys Cys Gly Glu Arg Val Val Ile Asn Ile Ser Gly Leu Arg Phe Glu
     50                  55                  60

Thr Gln Leu Lys Thr Leu Cys Gln Phe Pro Glu Thr Leu Leu Gly Asp
 65                  70                  75                  80
```

-continued

```
Pro Lys Arg Arg Met Arg Tyr Phe Asp Pro Leu Arg Asn Glu Tyr Phe
                85                  90                  95
Phe Asp Arg Asn Arg Pro Ser Phe Asp Ala Ile Leu Tyr Tyr Tyr Gln
            100                 105                 110
Ser Gly Gly Arg Ile Arg Arg Pro Val Asn Val Pro Ile Asp Ile Phe
        115                 120                 125
Ser Glu Glu Ile Arg Phe Tyr Gln Leu Gly Glu Ala Met Glu Lys
    130                 135                 140
Phe Arg Glu Asp Glu Gly Phe Leu Arg Glu Glu Arg Pro Leu Pro
145                 150                 155                 160
Arg Arg Asp Phe Gln Arg Gln Val Trp Leu Phe Glu Tyr Pro Glu
                165                 170                 175
Ser Ser Gly Pro Ala Arg Gly Ile Ala Ile Val Ser Val Leu Val Ile
            180                 185                 190
Leu Ile Ser Ile Val Ile Phe Cys Leu Glu Thr Leu Pro Glu Phe Arg
        195                 200                 205
Asp Glu Lys Asp Tyr Pro Ala Ser Thr Ser Gln Asp Ser Phe Glu Ala
    210                 215                 220
Ala Gly Asn Ser Thr Ser Gly Ser Arg Ala Gly Ala Ser Ser Phe Ser
225                 230                 235                 240
Asp Pro Phe Phe Val Val Glu Thr Leu Cys Ile Ile Trp Phe Ser Phe
                245                 250                 255
Glu Leu Leu Val Arg Phe Phe Ala Cys Pro Ser Lys Ala Thr Phe Ser
            260                 265                 270
Arg Asn Ile Met Asn Leu Ile Asp Ile Val Ala Ile Pro Tyr Phe
        275                 280                 285
Ile Thr Leu Gly Thr Glu Leu Ala Glu Arg Gln Gly Asn Gly Gln Gln
    290                 295                 300
Ala Met Ser Leu Ala Ile Leu Arg Val Ile Arg Leu Val Arg Val Phe
305                 310                 315                 320
Arg Ile Phe Lys Leu Ser Arg His Ser Lys Gly Leu Gln Ile Leu Gly
                325                 330                 335
Gln Thr Leu Lys Ala Ser Met Arg Glu Leu Gly Leu Leu Ile Phe Phe
            340                 345                 350
Leu Phe Ile Gly Val Ile Leu Phe Ser Ala Val Tyr Phe Ala Glu
        355                 360                 365
Ala Asp Asp Pro Thr Ser Gly Phe Ser Ser Ile Pro Asp Ala Phe Trp
    370                 375                 380
Trp Ala Val Val Thr Met Thr Thr Val Gly Tyr Gly Asp Met Trp Pro
385                 390                 395                 400
Val Thr Ile Gly Gly Lys Ile Val Gly Ser Leu Cys Ala Ile Ala Gly
                405                 410                 415
Val Leu Thr Ile Ala Leu Pro Val Pro Val Ile Val Ser Asn Phe Asn
            420                 425                 430
Tyr Phe Tyr His Arg Glu Thr Glu Gly Glu Glu Gln Ser Gln Tyr Met
        435                 440                 445
His Val Gly Ser Cys Gln His Leu Ser Ser Ala Glu Glu Leu Arg
    450                 455                 460
Lys Ala Arg Ser Asn Ser Thr Leu Ser Lys Ser Glu Tyr Met Val Ile
465                 470                 475                 480
Glu Glu Gly Gly Met Asn His Ser Ala Phe Pro Gln Thr Pro Phe Lys
                485                 490                 495
Thr Gly Asn Ser Thr Ala Thr Cys Thr Thr Asn Asn Pro Asn Ser
            500                 505                 510
```

Cys Val Asn Ile Lys Lys Ile Phe Thr Asp Val
        515                 520

<210> SEQ ID NO 3
<211> LENGTH: 1572
<212> TYPE: DNA
<213> ORGANISM: Homo sapiens

<400> SEQUENCE: 3

| | | |
|---|---|---|
| atgaccgtgg tgcccgggga ccacctgctg agccggagg tggccgatgg tggaggggcc | 60 |
| ccgcctcaag gcggctgtgg cggcggcggc tgcgaccgct acgagccgct gccgccctca | 120 |
| ctgccggccg cgggcgagca ggactgctgc ggggagcgcg tggtcatcaa catctccggg | 180 |
| ctgcgcttcg agacgcagct gaagaccctt tgccagttcc ccagacgct gctgggcgac | 240 |
| cccaagcggc gcatgaggta cttcgacccg ctccgcaacg agtacttctt cgaccgcaac | 300 |
| cggcccagct cgacgccat cctctactac tatcagtccg gggccgcat ccgccggccg | 360 |
| gtcaacgtgc ccatcgacat tttctccgag gagatccgct tctaccagct gggcgaggag | 420 |
| gccatggaga gttccgcga ggacgagggc ttcctgcggg aggaggagcg gcccttgccc | 480 |
| cgccgcgact ccagcgcca ggtgtggctg ctcttcgagt accccgagag ctccgggccg | 540 |
| gcccggggca tcgccatcgt gtccgtgctg gtcatcctca tctccattgt catcttctgc | 600 |
| ctggagacgc tgccggagtt ccgcgacgag aaggactacc ccgcctcgac gtcgcaggac | 660 |
| tcattcgaag cagccggcaa cagcacgtcg ggtcccgcg caggagcctc cagcttctcc | 720 |
| gatcccttct tcgtggtgga gacgctgtgc atcatctggt tctccttcga actgctggtg | 780 |
| cggttcttcg cttgtcctag caaagccacc ttctcgcgaa acatcatgaa cctgatcgac | 840 |
| attgtggcca tcattcctta ttttatcact ctgggtaccg agctggccga acgacagggc | 900 |
| aatggacagc aggccatgtc tctggccatc ctgagggtca tccgcctggt aagggtcttc | 960 |
| cgcatcttca gctgtcgcg ccactccaag gggctgcaga tcctcgggca aacgctgaag | 1020 |
| gcgtccatgc gggagctggg attgctcatc ttcttcctct ttattggggt catcctttttc | 1080 |
| tccagcgcgg tctactttgc cgaggcagac gaccccactt caggtttcag cagcatcccg | 1140 |
| gatgccttct ggtgggcagt ggtaaccatg acaacagtgg gttacggcga tatgcaccca | 1200 |
| gtgaccatag ggggcaagat tgtgggatct ctctgtgcca tcgccggtgt cttgaccatc | 1260 |
| gcattgccag ttcccgtgat tgtttccaac ttcaattact tctaccaccg ggagacagaa | 1320 |
| ggggaagagc aatcccagta catgcacgtg ggaagttgcc agcacctctc ctcttcagcc | 1380 |
| gaggagctcc gaaaagcaag gagtaactcg actctgagta agtcggagta tatggtgatc | 1440 |
| gaagagggg gtatgaacca tagcgctttc ccccagaccc ctttcaaaac gggcaattcc | 1500 |
| actgccacct gcaccacgaa caataatccc aactcttgtg tcaacatcaa aaagatattc | 1560 |
| accgatgttt aa | 1572 |

<210> SEQ ID NO 4
<211> LENGTH: 523
<212> TYPE: PRT
<213> ORGANISM: Homo sapiens

<400> SEQUENCE: 4

Met Thr Val Val Pro Gly Asp His Leu Leu Glu Pro Glu Val Ala Asp
1               5                   10                  15

Gly Gly Gly Ala Pro Pro Gln Gly Gly Cys Gly Gly Gly Cys Asp
            20                  25                  30

-continued

```
Arg Tyr Glu Pro Leu Pro Pro Ser Leu Pro Ala Ala Gly Glu Gln Asp
         35                  40                  45
Cys Cys Gly Glu Arg Val Val Ile Asn Ile Ser Gly Leu Arg Phe Glu
 50                  55                  60
Thr Gln Leu Lys Thr Leu Cys Gln Phe Pro Glu Thr Leu Leu Gly Asp
 65                  70                  75                  80
Pro Lys Arg Arg Met Arg Tyr Phe Asp Pro Leu Arg Asn Glu Tyr Phe
                 85                  90                  95
Phe Asp Arg Asn Arg Pro Ser Phe Asp Ala Ile Leu Tyr Tyr Tyr Gln
                100                 105                 110
Ser Gly Gly Arg Ile Arg Arg Pro Val Asn Val Pro Ile Asp Ile Phe
                115                 120                 125
Ser Glu Glu Ile Arg Phe Tyr Gln Leu Gly Glu Glu Ala Met Glu Lys
        130                 135                 140
Phe Arg Glu Asp Glu Gly Phe Leu Arg Glu Glu Arg Pro Leu Pro
145                 150                 155                 160
Arg Arg Asp Phe Gln Arg Gln Val Trp Leu Leu Phe Glu Tyr Pro Glu
                165                 170                 175
Ser Ser Gly Pro Ala Arg Gly Ile Ala Ile Val Ser Val Leu Val Ile
                180                 185                 190
Leu Ile Ser Ile Val Ile Phe Cys Leu Glu Thr Leu Pro Glu Phe Arg
        195                 200                 205
Asp Glu Lys Asp Tyr Pro Ala Ser Thr Ser Gln Asp Ser Phe Glu Ala
        210                 215                 220
Ala Gly Asn Ser Thr Ser Gly Ser Arg Ala Gly Ala Ser Ser Phe Ser
225                 230                 235                 240
Asp Pro Phe Phe Val Glu Thr Leu Cys Ile Ile Trp Phe Ser Phe
                245                 250                 255
Glu Leu Leu Val Arg Phe Phe Ala Cys Pro Ser Lys Ala Thr Phe Ser
                260                 265                 270
Arg Asn Ile Met Asn Leu Ile Asp Ile Val Ala Ile Ile Pro Tyr Phe
        275                 280                 285
Ile Thr Leu Gly Thr Glu Leu Ala Glu Arg Gln Gly Asn Gly Gln Gln
        290                 295                 300
Ala Met Ser Leu Ala Ile Leu Arg Val Ile Arg Leu Val Arg Val Phe
305                 310                 315                 320
Arg Ile Phe Lys Leu Ser Arg His Ser Lys Gly Leu Gln Ile Leu Gly
                325                 330                 335
Gln Thr Leu Lys Ala Ser Met Arg Glu Leu Gly Leu Leu Ile Phe Phe
                340                 345                 350
Leu Phe Ile Gly Val Ile Leu Phe Ser Ser Ala Val Tyr Phe Ala Glu
        355                 360                 365
Ala Asp Asp Pro Thr Ser Gly Phe Ser Ser Ile Pro Asp Ala Phe Trp
        370                 375                 380
Trp Ala Val Val Thr Met Thr Thr Val Gly Tyr Gly Asp Met His Pro
385                 390                 395                 400
Val Thr Ile Gly Gly Lys Ile Val Gly Ser Leu Cys Ala Ile Ala Gly
                405                 410                 415
Val Leu Thr Ile Ala Leu Pro Val Pro Val Ile Val Ser Asn Phe Asn
                420                 425                 430
Tyr Phe Tyr His Arg Glu Thr Glu Gly Glu Glu Gln Ser Gln Tyr Met
        435                 440                 445
His Val Gly Ser Cys Gln His Leu Ser Ser Ser Ala Glu Glu Leu Arg
        450                 455                 460
```

Lys Ala Arg Ser Asn Ser Thr Leu Ser Lys Ser Glu Tyr Met Val Ile
465                 470                 475                 480

Glu Glu Gly Gly Met Asn His Ser Ala Phe Pro Gln Thr Pro Phe Lys
            485                 490                 495

Thr Gly Asn Ser Thr Ala Thr Cys Thr Thr Asn Asn Pro Asn Ser
        500                 505                 510

Cys Val Asn Ile Lys Lys Ile Phe Thr Asp Val
        515                 520

<210> SEQ ID NO 5
<211> LENGTH: 1572
<212> TYPE: DNA
<213> ORGANISM: Homo sapiens
<220> FEATURE:
<221> NAME/KEY: misc_feature
<223> OTHER INFORMATION: H399T mutant

<400> SEQUENCE: 5

| | | |
|---|---|---|
| atgaccgtgg tgcccgggga ccacctgctg gagccggagg tggccgatgg tggaggggcc | 60 |
| ccgcctcaag gcggctgtgg cggcggcggc tgcgaccgct acgagccgct gccgccctca | 120 |
| ctgccggccg cgggcgagca ggactgctgc ggggagcgcg tggtcatcaa catctccggg | 180 |
| ctgcgcttcg agacgcagct gaagacccct tgccagttcc ccagagacgct gctgggcgac | 240 |
| cccaagcggc gcatgaggta cttcgacccg ctccgcaacg agtacttctt cgaccgcaac | 300 |
| cggcccagct tcgacgccat cctctactac tatcagtccg ggggccgcat ccgccggccg | 360 |
| gtcaacgtgc ccatcgacat tttctccgag gagatccgct ctaccagct gggcgaggag | 420 |
| gccatggaga agttccgcga ggacgagggc ttcctgcggg aggaggagcg gcccttgccc | 480 |
| cgccgcgact ccagcgcca ggtgtggctg ctcttcgagt accccgagag ctccggggccg | 540 |
| gcccggggca tcgccatcgt gtccgtgctg gtcatcctca tctccattgt catcttctgc | 600 |
| ctggagacgc tgccggagtt ccgcgacgag aaggactacc ccgcctcgac gtcgcaggac | 660 |
| tcattcgaag cagccggcaa cagcacgtcg gggtcccgcg caggagcctc cagcttctcc | 720 |
| gatcccttct tcgtggtgga gacgctgtgc atcatctggt tctccttcga actgctggtg | 780 |
| cggttcttcg cttgtcctag caaagccacc ttctcgcgaa acatcatgaa cctgatcgac | 840 |
| attgtggcca tcattcctta ttttatcact ctgggtaccg agctggccga acgacagggc | 900 |
| aatggacagc aggccatgtc tctggccatc ctgagggtca tccgcctggt aagggtcttc | 960 |
| cgcatcttca gctgtcgcg ccactccaag gggctgcaga tcctcgggca aacgctgaag | 1020 |
| gcgtccatgc gggagctggg attgctcatc ttcttcctct ttattggggt catccttttc | 1080 |
| tccagcgcgt tctactttgc cgaggcagac gaccccactt caggtttcag cagcatcccg | 1140 |
| gatgccttct ggtgggcagt ggtaaccatg acaacagtgg ttacggcga tatgacccca | 1200 |
| gtgaccatag ggggcaagat tgtgggatct ctctgtgcca tcgccggtgt cttgaccatc | 1260 |
| gcattgccag ttcccgtgat tgtttccaac ttcaattact tctaccaccg ggagacagaa | 1320 |
| ggggaagagc aatcccagta catgcacgtg ggaagttgcc agcacctctc ctcttcagcc | 1380 |
| gaggagctcc gaaaagcaag gagtaactcg actctgagta agtcggagta tatggtgatc | 1440 |
| gaagaggggg gtatgaacca tagcgctttc ccccagaccc cttttcaaaac gggcaattcc | 1500 |
| actgccacct gcaccacgaa caataatccc aactcttgtg tcaacatcaa aaagatattc | 1560 |
| accgatgttt aa | 1572 |

<210> SEQ ID NO 6

-continued

```
<211> LENGTH: 523
<212> TYPE: PRT
<213> ORGANISM: Homo sapiens
<220> FEATURE:
<221> NAME/KEY: misc_feature
<223> OTHER INFORMATION: H399T mutant

<400> SEQUENCE: 6

Met Thr Val Val Pro Gly Asp His Leu Leu Glu Pro Glu Val Ala Asp
1               5                   10                  15

Gly Gly Gly Ala Pro Pro Gln Gly Gly Cys Gly Gly Gly Gly Cys Asp
                20                  25                  30

Arg Tyr Glu Pro Leu Pro Ser Leu Pro Ala Ala Gly Glu Gln Asp
        35                  40                  45

Cys Cys Gly Glu Arg Val Val Ile Asn Ile Ser Gly Leu Arg Phe Glu
50                  55                  60

Thr Gln Leu Lys Thr Leu Cys Gln Phe Pro Glu Thr Leu Leu Gly Asp
65                  70                  75                  80

Pro Lys Arg Arg Met Arg Tyr Phe Asp Pro Leu Arg Asn Glu Tyr Phe
                85                  90                  95

Phe Asp Arg Asn Arg Pro Ser Phe Asp Ala Ile Leu Tyr Tyr Tyr Gln
                100                 105                 110

Ser Gly Gly Arg Ile Arg Arg Pro Val Asn Val Pro Ile Asp Ile Phe
            115                 120                 125

Ser Glu Glu Ile Arg Phe Tyr Gln Leu Gly Glu Glu Ala Met Glu Lys
130                 135                 140

Phe Arg Glu Asp Glu Gly Phe Leu Arg Glu Glu Arg Pro Leu Pro
145                 150                 155                 160

Arg Arg Asp Phe Gln Arg Gln Val Trp Leu Leu Phe Glu Tyr Pro Glu
                165                 170                 175

Ser Ser Gly Pro Ala Arg Gly Ile Ala Ile Val Ser Val Leu Val Ile
                180                 185                 190

Leu Ile Ser Ile Val Ile Phe Cys Leu Glu Thr Leu Pro Glu Phe Arg
            195                 200                 205

Asp Glu Lys Asp Tyr Pro Ala Ser Thr Ser Gln Asp Ser Phe Glu Ala
210                 215                 220

Ala Gly Asn Ser Thr Ser Gly Ser Arg Ala Gly Ala Ser Ser Phe Ser
225                 230                 235                 240

Asp Pro Phe Phe Val Val Glu Thr Leu Cys Ile Ile Trp Phe Ser Phe
                245                 250                 255

Glu Leu Leu Val Arg Phe Phe Ala Cys Pro Ser Lys Ala Thr Phe Ser
                260                 265                 270

Arg Asn Ile Met Asn Leu Ile Asp Ile Val Ala Ile Ile Pro Tyr Phe
            275                 280                 285

Ile Thr Leu Gly Thr Glu Leu Ala Glu Arg Gln Gly Asn Gly Gln Gln
290                 295                 300

Ala Met Ser Leu Ala Ile Leu Arg Val Ile Arg Leu Val Arg Val Phe
305                 310                 315                 320

Arg Ile Phe Lys Leu Ser Arg His Ser Lys Gly Leu Gln Ile Leu Gly
                325                 330                 335

Gln Thr Leu Lys Ala Ser Met Arg Glu Leu Gly Leu Leu Ile Phe Phe
                340                 345                 350

Leu Phe Ile Gly Val Ile Leu Phe Ser Ser Ala Val Tyr Phe Ala Glu
            355                 360                 365

Ala Asp Asp Pro Thr Ser Gly Phe Ser Ser Ile Pro Asp Ala Phe Trp
370                 375                 380
```

```
Trp Ala Val Val Thr Met Thr Thr Val Gly Tyr Gly Asp Met Thr Pro
385                 390                 395                 400

Val Thr Ile Gly Gly Lys Ile Val Gly Ser Leu Cys Ala Ile Ala Gly
            405                 410                 415

Val Leu Thr Ile Ala Leu Pro Val Pro Val Ile Val Ser Asn Phe Asn
                420                 425                 430

Tyr Phe Tyr His Arg Glu Thr Glu Gly Glu Glu Gln Ser Gln Tyr Met
            435                 440                 445

His Val Gly Ser Cys Gln His Leu Ser Ser Ser Ala Glu Glu Leu Arg
                450                 455                 460

Lys Ala Arg Ser Asn Ser Thr Leu Ser Lys Ser Glu Tyr Met Val Ile
465                 470                 475                 480

Glu Glu Gly Gly Met Asn His Ser Ala Phe Pro Gln Thr Pro Phe Lys
                485                 490                 495

Thr Gly Asn Ser Thr Ala Thr Cys Thr Thr Asn Asn Pro Asn Ser
                500                 505                 510

Cys Val Asn Ile Lys Lys Ile Phe Thr Asp Val
                515                 520
```

<210> SEQ ID NO 7
<211> LENGTH: 1572
<212> TYPE: DNA
<213> ORGANISM: Homo sapiens
<220> FEATURE:
<221> NAME/KEY: misc_feature
<223> OTHER INFORMATION: A413V mutant

<400> SEQUENCE: 7

```
atgaccgtgg tgcccgggga ccacctgctg gagccggagg tggccgatgg tggaggggcc      60
ccgcctcaag gcggctgtgg cggcggcggc tgcgaccgct acgagccgct gccgccctca     120
ctgccggccg cgggcgagca ggactgctgc ggggagcgcg tggtcatcaa catctccggg     180
ctgcgcttcg agacgcagct gaagacccct tgccagttcc ccgagacgct gctgggcgac     240
cccaagcggc gcatgaggta cttcgacccg ctccgcaacg agtacttctt cgaccgcaac     300
cggcccagct tcgacgccat cctctactac tatcagtccg ggggccgcat ccgccggccg     360
gtcaacgtgc ccatcgacat tttctccgag gagatccgct tctaccagct gggcgaggag     420
gccatggaga agttccgcga ggacgagggc ttcctgcggg aggaggagcg gcccttgccc     480
cgccgcgact ccagcgcca ggtgtggctg ctcttcgagt accccgagag ctccggggccg     540
gcccggggca tcgccatcgt gtccgtgctg gtcatcctca tctccattgt catcttctgc     600
ctggagacgc tgccggagtt ccgcgacgag aaggactacc ccgcctcgac gtcgcaggac     660
tcattcgaag cagccggcaa cagcacgtcg gggtcccgcg caggagcctc cagcttctcc     720
gatccctcct tcgtggtgga cacgctgtgc atcatctggt tctccttcga actgctggtg     780
cggttcttcg cttgtcctag caaagccacc ttctcgcgaa acatcatgaa cctgatcgac     840
attgtggcca tcattcctta ttttatcact ctgggtaccg agctggccga acgacagggc     900
aatgacagc aggccatgtc tctggccatc ctgagggtca tccgcctggt aagggtcttc     960
cgcatcttca gctgtcgcg ccactccaag gggctgcaga tcctcggca aacgctgaag    1020
gcgtccatgc gggagctggg attgctcatc ttcttcctct ttattgggt catccttttc    1080
tccagcgcgg tctactttgc cgaggcagac gacccccactt caggttttcag cagcatcccg    1140
gatgccttct ggtgggcagt ggtaaccatg acaacagtgg gttacggcga tatgcaccca    1200
gtgaccatag ggggcaagat tgtgggatct ctctgtgtca tcgccggtgt cttgaccatc    1260
```

```
gcattgccag ttcccgtgat tgtttccaac ttcaattact tctaccaccg ggagacagaa    1320
ggggaagagc aatcccagta catgcacgtg ggaagttgcc agcacctctc ctcttcagcc    1380
gaggagctcc gaaaagcaag gagtaactcg actctgagta agtcggagta tatggtgatc    1440
gaagaggggg gtatgaacca tagcgctttc ccccagaccc ctttcaaaac gggcaattcc    1500
actgccacct gcaccacgaa caataatccc aactcttgtg tcaacatcaa aaagatattc    1560
accgatgttt aa                                                        1572
```

<210> SEQ ID NO 8
<211> LENGTH: 523
<212> TYPE: PRT
<213> ORGANISM: Homo sapiens
<220> FEATURE:
<221> NAME/KEY: misc_feature
<223> OTHER INFORMATION: A413V mutant

<400> SEQUENCE: 8

```
Met Thr Val Val Pro Gly Asp His Leu Leu Glu Pro Glu Val Ala Asp
1               5                   10                  15

Gly Gly Gly Ala Pro Pro Gln Gly Gly Cys Gly Gly Gly Gly Cys Asp
            20                  25                  30

Arg Tyr Glu Pro Leu Pro Pro Ser Leu Pro Ala Ala Gly Glu Gln Asp
        35                  40                  45

Cys Cys Gly Glu Arg Val Val Ile Asn Ile Ser Gly Leu Arg Phe Glu
    50                  55                  60

Thr Gln Leu Lys Thr Leu Cys Gln Phe Pro Glu Thr Leu Leu Gly Asp
65                  70                  75                  80

Pro Lys Arg Arg Met Arg Tyr Phe Asp Pro Leu Arg Asn Glu Tyr Phe
                85                  90                  95

Phe Asp Arg Asn Arg Pro Ser Phe Asp Ala Ile Leu Tyr Tyr Tyr Gln
            100                 105                 110

Ser Gly Gly Arg Ile Arg Arg Pro Val Asn Val Pro Ile Asp Ile Phe
        115                 120                 125

Ser Glu Glu Ile Arg Phe Tyr Gln Leu Gly Glu Glu Ala Met Glu Lys
    130                 135                 140

Phe Arg Glu Asp Glu Gly Phe Leu Arg Glu Glu Arg Pro Leu Pro
145                 150                 155                 160

Arg Arg Asp Phe Gln Arg Gln Val Trp Leu Leu Phe Glu Tyr Pro Glu
                165                 170                 175

Ser Ser Gly Pro Ala Arg Gly Ile Ala Ile Val Ser Val Leu Val Ile
            180                 185                 190

Leu Ile Ser Ile Val Ile Phe Cys Leu Glu Thr Leu Pro Glu Phe Arg
        195                 200                 205

Asp Glu Lys Asp Tyr Pro Ala Ser Thr Ser Gln Asp Ser Phe Glu Ala
    210                 215                 220

Ala Gly Asn Ser Thr Ser Gly Ser Arg Ala Gly Ala Ser Ser Phe Ser
225                 230                 235                 240

Asp Pro Phe Phe Val Val Glu Thr Leu Cys Ile Ile Trp Phe Ser Phe
                245                 250                 255

Glu Leu Leu Val Arg Phe Phe Ala Cys Pro Ser Lys Ala Thr Phe Ser
            260                 265                 270

Arg Asn Ile Met Asn Leu Ile Asp Ile Val Ala Ile Ile Pro Tyr Phe
        275                 280                 285

Ile Thr Leu Gly Thr Glu Leu Ala Glu Arg Gln Gly Asn Gly Gln Gln
    290                 295                 300
```

```
Ala Met Ser Leu Ala Ile Leu Arg Val Ile Arg Leu Val Arg Val Phe
305                 310                 315                 320

Arg Ile Phe Lys Leu Ser Arg His Ser Lys Gly Leu Gln Ile Leu Gly
            325                 330                 335

Gln Thr Leu Lys Ala Ser Met Arg Glu Leu Gly Leu Leu Ile Phe Phe
            340                 345                 350

Leu Phe Ile Gly Val Ile Leu Phe Ser Ser Ala Val Tyr Phe Ala Glu
        355                 360                 365

Ala Asp Asp Pro Thr Ser Gly Phe Ser Ser Ile Pro Asp Ala Phe Trp
370                 375                 380

Trp Ala Val Val Thr Met Thr Thr Val Gly Tyr Gly Asp Met His Pro
385                 390                 395                 400

Val Thr Ile Gly Gly Lys Ile Val Gly Ser Leu Cys Val Ile Ala Gly
            405                 410                 415

Val Leu Thr Ile Ala Leu Pro Val Pro Val Ile Val Ser Asn Phe Asn
            420                 425                 430

Tyr Phe Tyr His Arg Glu Thr Glu Gly Glu Glu Gln Ser Gln Tyr Met
        435                 440                 445

His Val Gly Ser Cys Gln His Leu Ser Ser Ser Ala Glu Glu Leu Arg
450                 455                 460

Lys Ala Arg Ser Asn Ser Thr Leu Ser Lys Ser Glu Tyr Met Val Ile
465                 470                 475                 480

Glu Glu Gly Gly Met Asn His Ser Ala Phe Pro Gln Thr Pro Phe Lys
            485                 490                 495

Thr Gly Asn Ser Thr Ala Thr Cys Thr Thr Asn Asn Asn Pro Asn Ser
            500                 505                 510

Cys Val Asn Ile Lys Lys Ile Phe Thr Asp Val
            515                 520

<210> SEQ ID NO 9
<211> LENGTH: 1572
<212> TYPE: DNA
<213> ORGANISM: Homo sapiens
<220> FEATURE:
<221> NAME/KEY: misc_feature
<223> OTHER INFORMATION: A413C mutant

<400> SEQUENCE: 9
atgaccgtgg tgcccgggga ccacctgctg gagccggagg tggccgatgg tggagggggcc        60 ccgcctcaag gcggctgtgg cggcggcggc tgcgaccgct acgagccgct gccgccctca       120
ctgccggccg cgggcgagca ggactgctgc ggggagcgcg tggtcatcaa catctccggg       180
ctgcgcttcg agacgcagct gaagacccct tgccagttcc ccgagacgct gctgggcgac       240
cccaagcggc gcatgaggta cttcgacccg ctccgcaacg agtacttctt cgaccgcaac       300
cggcccagct tcgacgccat cctctactac tatcagtccg ggggccgcat ccgccggccg       360
gtcaacgtgc ccatcgacat tttctccgag gagatccgct tctaccagct gggcgaggag       420
gccatggaga gttccgcga ggacgagggc ttcctgcggg aggaggagcg gcccttgccc       480
cgccgcgact ccagcgcca ggtgtggctg ctcttcgagt accccgagag ctccgggccg       540
gcccggggca tcgccatcgt gtccgtgctg gtcatcctca tctccattgt catcttctgc       600
ctggagacgc tgccggagtt ccgcgacgag aaggactacc ccgcctcgac gtcgcaggac       660
tcattcgaag cagccggcaa cagcacgtcg ggtccgcg caggagcctc cagcttctcc       720
gatcccttct tcgtggtgga gacgctgtgc atcatctggt tctccttcga actgctggtg       780
```

```
cggttcttcg cttgtcctag caaagccacc ttctcgcgaa acatcatgaa cctgatcgac    840
attgtggcca tcattcctta ttttatcact ctgggtaccg agctggccga acgacagggc    900
aatggacagc aggccatgtc tctggccatc ctgagggtca tccgcctggt aagggtcttc    960
cgcatcttca agctgtcgcg ccactccaag gggctgcaga tcctcgggca aacgctgaag   1020
gcgtccatgc gggagctggg attgctcatc ttcttcctct ttattggggt catccttttc   1080
tccagcgcgg tctactttgc cgaggcagac gaccccactt caggtttcag cagcatcccg   1140
gatgccttct ggtgggcagt ggtaaccatg acaacagtgg gttacggcga tatgcaccca   1200
gtgaccatag ggggcaagat tgtgggatct tctctgttgca tcgccggtgt cttgaccatc   1260
gcattgccag ttcccgtgat tgtttccaac ttcaattact tctaccaccg ggagacagaa   1320
ggggaagagc aatcccagta catgcacgtg ggaagttgcc agcacctctc ctcttcagcc   1380
gaggagctcc gaaaagcaag gagtaactcg actctgagta agtcggagta tatggtgatc   1440
gaagaggggg gtatgaacca tagcgctttc ccccagaccc ctttcaaaac gggcaattcc   1500
actgccacct gcaccacgaa caataatccc aactcttgtg tcaacatcaa aaagatattc   1560
accgatgttt aa                                                       1572
```

<210> SEQ ID NO 10
<211> LENGTH: 523
<212> TYPE: PRT
<213> ORGANISM: Homo sapiens

<400> SEQUENCE: 10

```
Met Thr Val Val Pro Gly Asp His Leu Leu Glu Pro Glu Val Ala Asp
1               5                   10                  15

Gly Gly Gly Ala Pro Pro Gln Gly Gly Cys Gly Gly Gly Gly Cys Asp
                20                  25                  30

Arg Tyr Glu Pro Leu Pro Pro Ser Leu Pro Ala Ala Gly Glu Gln Asp
            35                  40                  45

Cys Cys Gly Glu Arg Val Val Ile Asn Ile Ser Gly Leu Arg Phe Glu
        50                  55                  60

Thr Gln Leu Lys Thr Leu Cys Gln Phe Pro Glu Thr Leu Leu Gly Asp
65                  70                  75                  80

Pro Lys Arg Arg Met Arg Tyr Phe Asp Pro Leu Arg Asn Glu Tyr Phe
                85                  90                  95

Phe Asp Arg Asn Arg Pro Ser Phe Asp Ala Ile Leu Tyr Tyr Tyr Gln
            100                 105                 110

Ser Gly Gly Arg Ile Arg Arg Pro Val Asn Val Pro Ile Asp Ile Phe
        115                 120                 125

Ser Glu Glu Ile Arg Phe Tyr Gln Leu Gly Glu Glu Ala Met Glu Lys
130                 135                 140

Phe Arg Glu Asp Glu Gly Phe Leu Arg Glu Glu Arg Pro Leu Pro
145                 150                 155                 160

Arg Arg Asp Phe Gln Arg Gln Val Trp Leu Leu Phe Glu Tyr Pro Glu
                165                 170                 175

Ser Ser Gly Pro Ala Arg Gly Ile Ala Ile Val Ser Val Leu Val Ile
            180                 185                 190

Leu Ile Ser Ile Val Ile Phe Cys Leu Glu Thr Leu Pro Glu Phe Arg
        195                 200                 205

Asp Glu Lys Asp Tyr Pro Ala Ser Thr Ser Gln Asp Ser Phe Glu Ala
    210                 215                 220

Ala Gly Asn Ser Thr Ser Gly Ser Arg Ala Gly Ala Ser Ser Phe Ser
225                 230                 235                 240
```

```
Asp Pro Phe Phe Val Val Glu Thr Leu Cys Ile Ile Trp Phe Ser Phe
            245                 250                 255

Glu Leu Leu Val Arg Phe Phe Ala Cys Pro Ser Lys Ala Thr Phe Ser
        260                 265                 270

Arg Asn Ile Met Asn Leu Ile Asp Ile Val Ala Ile Ile Pro Tyr Phe
            275                 280                 285

Ile Thr Leu Gly Thr Glu Leu Ala Glu Arg Gln Gly Asn Gly Gln Gln
290                 295                 300

Ala Met Ser Leu Ala Ile Leu Arg Val Ile Arg Leu Val Arg Val Phe
305                 310                 315                 320

Arg Ile Phe Lys Leu Ser Arg His Ser Lys Gly Leu Gln Ile Leu Gly
                325                 330                 335

Gln Thr Leu Lys Ala Ser Met Arg Glu Leu Gly Leu Leu Ile Phe Phe
                340                 345                 350

Leu Phe Ile Gly Val Ile Leu Phe Ser Ser Ala Val Tyr Phe Ala Glu
            355                 360                 365

Ala Asp Asp Pro Thr Ser Gly Phe Ser Ser Ile Pro Asp Ala Phe Trp
        370                 375                 380

Trp Ala Val Val Thr Met Thr Thr Val Gly Tyr Gly Asp Met His Pro
385                 390                 395                 400

Val Thr Ile Gly Gly Lys Ile Val Gly Ser Leu Cys Cys Ile Ala Gly
                405                 410                 415

Val Leu Thr Ile Ala Leu Pro Val Pro Val Ile Val Ser Asn Phe Asn
            420                 425                 430

Tyr Phe Tyr His Arg Glu Thr Glu Gly Glu Glu Gln Ser Gln Tyr Met
        435                 440                 445

His Val Gly Ser Cys Gln His Leu Ser Ser Ser Ala Glu Glu Leu Arg
    450                 455                 460

Lys Ala Arg Ser Asn Ser Thr Leu Ser Lys Ser Glu Tyr Met Val Ile
465                 470                 475                 480

Glu Glu Gly Gly Met Asn His Ser Ala Phe Pro Gln Thr Pro Phe Lys
                485                 490                 495

Thr Gly Asn Ser Thr Ala Thr Cys Thr Thr Asn Asn Pro Asn Ser
                500                 505                 510

Cys Val Asn Ile Lys Lys Ile Phe Thr Asp Val
            515                 520
```

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11
gaagatctat gaccgtggtg ccc                                          23

<210> SEQ ID NO 12
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 12
ccggtcgact taaacatcgg tgaa                                         24

```
<210> SEQ ID NO 13
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 13
gaagatctat gaccgtggtg ccc                                            23

<210> SEQ ID NO 14
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 14
ccggaattcc ccactgttgt cat                                            23

<210> SEQ ID NO 15
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 15
ccggaattct tacggcgata tgtggccagt gac                                 33

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
ccggtcgact taaacatcgg tgaa                                           24

<210> SEQ ID NO 17
<211> LENGTH: 1532
<212> TYPE: DNA
<213> ORGANISM: Artificial sequence
<220> FEATURE:
<223> OTHER INFORMATION: A recombinant polynucleotide having the H399W
      mutation

<400> SEQUENCE: 17
atgaccgtgg tgcccgggga ccacctgctg gagccggagg tggccgatgg tggaggggcc     60
ccgcctcaag gcggctgtgg cggcggcggc tgcgaccgct acgagccgct gccgccctca    120
ctgccggccg cgggcgagca ggactgctgc ggggagcgcg tggtcatcaa catctccggg    180
ctgcgcttcg agacgcagct gaagacccct tgccagttcc cgagacgct gctgggcgac    240 cccaagcggc gcatgaggta cttcgacccg ctccgcaacg agtacttctt cgaccgcaac    300
cggcccagct tcgacgccat cctctactac tatcagtccg ggggccgcat ccgccggccg    360
gtcaacgtgc ccatcgacat tttctccgag agatccgct tctaccagct gggcgaggag    420
gccatggaga agttccgcga ggacgagggc ttcctgcggg aggaggagcg gccccttgccc   480 cgccgcgact ccagcgcca ggtgtggctg ctcttcgagt accccgagag ctccgggccg    540
gcccggggca tcgccatcgt gtccgtgctg gtcatcctca tctccattgt catcttctgc    600
ctggagacgc tgccggagtt ccgcgacgag aaggactacc ccgcctcgac gtcgcaggac    660
```

```
tcattcgaag cagccggcaa cagcacgtcg gggtcccgcg caggagcctc cagcttctcc    720
gatcccttct tcgtggtgga gacgctgtgc atcatctggt tctccttcga actgctggtg    780
cggttcttcg cttgtcctag caaagccacc ttctcgcgaa acatcatgaa cctgatcgac    840
attgtggcca tcattcctta ttttatcact ctgggtaccg agctggccga acgacagggc    900
aatggacagc aggccatgtc tctggccatc ctgagggtca tccgcctggt aagggtcttc    960
cgcatcttca agctgtcgcg ccactccaag gggctgcaga tcctcgggca aacgctgaag   1020
gcgtccatgc gggagctggg attgctcatc ttcttcctct ttattggggt catccttttc   1080
tccagcgcgg tctactttgc cgaggcagac gaccccactt caggtttcag cagcatcccg   1140
gatgccttct ggtgggcagt ggtaaccatg acaacagtgg ggaattctta cggcgatatg   1200
tggccagtga ccataggggg caagattgtg ggatctctct gtgccatcgc cggtgtcttg   1260
accatcgcat tgccagttcc cgtgattgtt tccaacttca attacttcta ccaccgggag   1320
acagaagggg aagagcaatc ccagtacatg cacgtgggaa gttgccagca cctctcctct   1380
tcagccgagg agctccgaaa agcaaggagt aactcgactc tgagtaagtc ggagtatatg   1440
gtgatcgaag agggggggtat gaaccatagc gctttccccc agacccctt caaaacgggc    1500
aattccactg ccacctgcac cacgaacaat aa                                 1532
```

<210> SEQ ID NO 18
<211> LENGTH: 510
<212> TYPE: PRT
<213> ORGANISM: Artificial sequence
<220> FEATURE:
<223> OTHER INFORMATION: A recombinant polypeptide having the H399W mutation

<400> SEQUENCE: 18

```
Met Thr Val Val Pro Gly Asp His Leu Leu Glu Pro Glu Val Ala Asp
 1               5                  10                  15

Gly Gly Gly Ala Pro Pro Gln Gly Gly Cys Gly Gly Gly Cys Asp
             20                  25                  30

Arg Tyr Glu Pro Leu Pro Pro Ser Leu Pro Ala Ala Gly Glu Gln Asp
         35                  40                  45

Cys Cys Gly Glu Arg Val Val Ile Asn Ile Ser Gly Leu Arg Phe Glu
     50                  55                  60

Thr Gln Leu Lys Thr Leu Cys Gln Phe Pro Glu Thr Leu Leu Gly Asp
 65                  70                  75                  80

Pro Lys Arg Arg Met Arg Tyr Phe Asp Pro Leu Arg Asn Glu Tyr Phe
                 85                  90                  95

Phe Asp Arg Asn Arg Pro Ser Phe Asp Ala Ile Leu Tyr Tyr Tyr Gln
            100                 105                 110

Ser Gly Gly Arg Ile Arg Arg Pro Val Asn Val Pro Ile Asp Ile Phe
        115                 120                 125

Ser Glu Glu Ile Arg Phe Tyr Gln Leu Gly Glu Glu Ala Met Glu Lys
    130                 135                 140

Phe Arg Glu Asp Glu Gly Phe Leu Arg Glu Glu Arg Pro Leu Pro
145                 150                 155                 160

Arg Arg Asp Phe Gln Arg Gln Val Trp Leu Leu Phe Glu Tyr Pro Glu
                165                 170                 175

Ser Ser Gly Pro Ala Arg Gly Ile Ala Ile Val Ser Val Leu Val Ile
            180                 185                 190

Leu Ile Ser Ile Val Ile Phe Cys Leu Glu Thr Leu Pro Glu Phe Arg
        195                 200                 205
```

```
                                   -continued
Asp Glu Lys Asp Tyr Pro Ala Ser Thr Ser Gln Asp Ser Phe Glu Ala
    210                 215                 220

Ala Gly Asn Ser Thr Ser Gly Ser Arg Ala Gly Ala Ser Ser Phe Ser
225                 230                 235                 240

Asp Pro Phe Phe Val Val Glu Thr Leu Cys Ile Ile Trp Phe Ser Phe
                245                 250                 255

Glu Leu Leu Val Arg Phe Phe Ala Cys Pro Ser Lys Ala Thr Phe Ser
            260                 265                 270

Arg Asn Ile Met Asn Leu Ile Asp Ile Val Ala Ile Ile Pro Tyr Phe
        275                 280                 285

Ile Thr Leu Gly Thr Glu Leu Ala Glu Arg Gln Gly Asn Gly Gln Gln
    290                 295                 300

Ala Met Ser Leu Ala Ile Leu Arg Val Ile Arg Leu Val Arg Val Phe
305                 310                 315                 320

Arg Ile Phe Lys Leu Ser Arg His Ser Lys Gly Leu Gln Ile Leu Gly
                325                 330                 335

Gln Thr Leu Lys Ala Ser Met Arg Glu Leu Gly Leu Leu Ile Phe Phe
            340                 345                 350

Leu Phe Ile Gly Val Ile Leu Phe Ser Ser Ala Val Tyr Phe Ala Glu
        355                 360                 365

Ala Asp Asp Pro Thr Ser Gly Phe Ser Ser Ile Pro Asp Ala Phe Trp
    370                 375                 380

Trp Ala Val Val Thr Met Thr Thr Val Gly Asn Ser Tyr Gly Asp Met
385                 390                 395                 400

Trp Pro Val Thr Ile Gly Gly Lys Ile Val Gly Ser Leu Cys Ala Ile
                405                 410                 415

Ala Gly Val Leu Thr Ile Ala Leu Pro Val Pro Val Ile Val Ser Asn
            420                 425                 430

Phe Asn Tyr Phe Tyr His Arg Glu Thr Glu Gly Glu Glu Gln Ser Gln
        435                 440                 445

Tyr Met His Val Gly Ser Cys Gln His Leu Ser Ser Ser Ala Glu Glu
    450                 455                 460

Leu Arg Lys Ala Arg Ser Asn Ser Thr Leu Ser Lys Ser Glu Tyr Met
465                 470                 475                 480

Val Ile Glu Glu Gly Gly Met Asn His Ser Ala Phe Pro Gln Thr Pro
                485                 490                 495

Phe Lys Thr Gly Asn Ser Thr Ala Thr Cys Thr Thr Asn Asn
            500                 505                 510
```

POLYNUCLEOTIDES AND POLYPEPTIDE OF HUMAN KV1.3, COMPOSITIONS COMPRISING SAME AND METHODS OF USING SAME

RELATED APPLICATIONS

This Application is a National Phase of PCT Patent Application No. PCT/IL2006/001431 having International filing date of Dec. 12, 2006, which claims the benefit of U.S. Provisional Patent Application No. 60/750,342 filed on Dec. 15, 2005. The contents of the above Applications are all incorporated herein by reference.

FIELD AND BACKGROUND OF THE INVENTION

The present invention relates to polynucleotide and polypeptides of Human Kv1.3, compositions comprising same and methods of using them.

Ion channels are proteins embedded within the cell membrane that control the selective flux of ions across the membrane, thereby allowing the rapid movement of ions during electrical signaling processes. Because ion concentrations are directly involved in the electrical activity of excitable cells (e.g., neurons), the functioning (or malfunctioning) of ion channels can substantially control the electrical properties and behavior of such cells. Indeed, a variety of disorders, broadly termed as "channelopathies," are believed to be linked to ion channel insufficiencies or dysfunctions.

Ion channels are referred to as "gated" if they can be opened or closed. The basic types of gated ion channels include a) ligand-gated channels, b) mechanically gated channels and c) voltage-gated channels. In particular, voltage-gated channels are found in neurons and muscle cells. Voltage-gated ion channels open or close in response to changes in the potential differences across the plasma membrane.

Voltage-gated and ligand gated ion channels have been mapped in various excitable tissues including secretory tissues (e.g., kidney, liver, pancreas), the heart and the neural tissues (e.g., autonomic neurons). Medications that are directed to ion channels account for a major pharmaceutical market segment. Such drugs increase or decrease the flux of ions through those ion channels to bring about desired therapeutic effects.

Modification of the excitability of cardiac tissues by overexpression of specific ion channels have been previously described (Hoppe U C, Marban E, and Johns D C. Molecular dissection of cardiac repolarization by in vivo Kv4.3 gene transfer. *J Clin Invest* 105: 1077-1084, 2000). Briefly, overexpression of the KV1.3 gene was shown to significantly shorten the action potential duration in myocytes having a normal action potential duration at baseline.

Alternatively, transplantation of cells overexpressing ion channels was also suggested for excitable tissue modulation (Yair Feld, Meira Melamed-Frank, Izhak Kehat, Dror Tal, Shimon Marom, Lior Gepstein. Electrophysiological Modulation of Cardiomyocytic Tissue by Transfected Fibroblasts Expressing Potassium Channels: A Novel Strategy to Manipulate Excitability. Circulation. 2002 January; 105: 522-529; see PCT Publication No. WO2006/018836).

Prolongation of the refractory period is one strategy for the treatment of cardiac arrhythmias. The voltage gated Kv1.3 channel expresses a long tail current causing it to be attractive as a potential modulator of the cardiac effective refractory period (ERP) when overexpressed by cardiomyocytes or other cells electrically coupled with cardiomyocytes. It was previously demonstrated that rat Kv1.3 channel in which the histidine at position 401 was replaced by tryptophan (Kv1.3 H401 W) introduced a rapid inactivation property to the channel (Kupper J, Bowlby R M, Marom S, Levitan BT. Intracellular and extracellular amino acids that influence C-type inactivation and its modulation in a voltage-dependent potassium channel. Eur J. Physiol. 1995; 430: 1-11). Preliminary analysis suggested that the effect of the mutation is caused by slowing down of the recovery rate from inactivation. In this channel recovery from inactivation involved passing through the open state. It was demonstrated that the mutant channel has significantly long tail current (American Society of Gene Therapy 8th Annual Meeting. Refractory Period Prolongation by Fibroblasts Overexpressing the Mutant Kv1.3H401W Channel in Computer Simulation and Pig Hearts. Shabtay A, Bresler T, Yankelson L, Gepstein L, Marom S, and Feld Y. 2005.). Shabtay et al also demonstrated stronger effect in prolonging of the refractory period of pig hearts at specific loci by transplantation of fibroblasts overexpressing the rat Kv1.3H401W vs. the wild type Kv1.3 channel by computer simulation and in vivo experiments.

Interestingly, reported mutations in the S6 domain of human Kv1.3 (H399T and optionally A413C) were shown to mediate an opposite effect to that of the 11401 W, essentially reduction in the C-type inactivation of the channel and faster recovery rate.

In another report A413V mutation of hKv1.3 was shown to actually increase inactivation of the channel, however use of same for the treatment of various pathophysiologies has never been suggested [Panyi (1995) Biophysical Journal 69: 896-903].

There is thus a widely recognized need for and it would be highly advantageous to have hKv1.3 mutants with increased C-type inactivation rate and methods of using same in human therapy and drug screening.

SUMMARY OF THE INVENTION

According to one aspect of the present invention there is provided an isolated polypeptide comprising, contiguously, a first amino acid sequence being at least 90% homologous to amino acid coordinates 1-398 of SEQ ID NO: 2, a tryptophan residue and a second amino acid sequence being at least 90% homologous to amino acid coordinates 400-523 of SEQ ID NO:2.

According to further features in preferred embodiments of the invention described below, the polypeptide comprises a voltage-gated potassium channel activity.

According to still further features in the described preferred embodiments an inactivation rate of the potassium channel is faster than that of SEQ ID NO: 4 or 6.

According to another aspect of the present invention there is provided an isolated polypeptide comprising an amino acid sequence as set forth in SEQ ID NO: 2.

According to yet another aspect of the present invention there is provided a peptide of at least 5 amino acids in length derived from the isolated polypeptide and which comprises the tryptophan residue.

According to still another aspect of the present invention there is provided an antibody comprising an antigen recognition domain capable of specifically binding the isolated polypeptide and incapable of binding a human Kv1.3 polypeptide devoid of the tryptophan residue (SEQ ID NO: 4).

According to an additional aspect of the present invention there is provided an isolated polynucleotide comprising a nucleic acid sequence encoding the polypeptide.

According to yet an additional aspect of the present invention there is provided an isolated polynucleotide comprising a nucleic acid sequence encoding the polypeptide.

According to still an additional aspect of the present invention there is provided a nucleic acid construct comprising the polynucleotide.

According to still further features in the described preferred embodiments the nucleic acid construct further comprising a promoter for regulating expression of the polynucleotide.

According to a further aspect of the present invention there is provided an isolated cell comprising the nucleic acid construct.

According to still further features in the described preferred embodiments the cell is selected from the group consisting of a fibroblast, a stem cell, a myoblast, a glial cell and an endothelial cell.

According to yet a further aspect of the present invention there is provided an oligonucleotide capable of specifically hybridizing to the isolated and not to a polynucleotide encoding a Kv1.3 polypeptide devoid of the tryptophan residue (SEQ ID NO: 4) under stringent hybridization conditions.

According to still a further aspect of the present invention there is provided a pharmaceutical composition comprising as an active ingredient a polynucleotide which comprises a nucleic acid sequence encoding an hKv1.3 polypeptide mutant having a voltage-gated potassium channel activity exhibiting an altered inactivation rate as compared to wild type hKv1.3 (SEQ ID NO: 4).

According to still further features in the described preferred embodiments the hKv1.3 polypeptide mutant comprises SEQ ID NO: 2, 6, 8 or 10.

According to still a further aspect of the present invention there is provided a pharmaceutical composition comprising as an active ingredient a cell which comprises the polynucleotide.

According to still a further aspect of the present invention there is provided use of a polynucleotide which comprises a nucleic acid sequence encoding an hKv1.3 polypeptide mutant having a voltage-gated potassium channel activity exhibiting an altered inactivation rate compared to wild type hKv1.3 or a cell expressing the polynucleotide for the manufacture of a medicament identified for treating a medical condition associated with ion channel insufficiency.

According to still a further aspect of the present invention there is provided a method of identifying an agent capable of regulating an activity of a voltage-gated potassium channel, the method comprising determining an activity of the Kv1.3 polypeptide in the presence and absence of the agent, wherein a change in the activity of the Kv1.3 polypeptide is indicative of an agent capable of regulating the activity of the voltage-gated potassium channel.

The present invention successfully addresses the shortcomings of the presently known configurations by providing polynucleotide and polypeptide sequences of hKv1.3, pharmaceutical compositions which comprise the same and methods of use.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
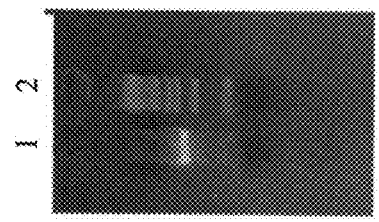

FIG. 1 is a photomicrograph showing PCR amplification of Kv1.3 gene (1571 bp). Lane 1—hKV1.3 wild type (wt) fragment of 1571 bp. Lane 2—2.1 kb DNA Ladder (Biolabs; cat#N3232S).

Figure 2:
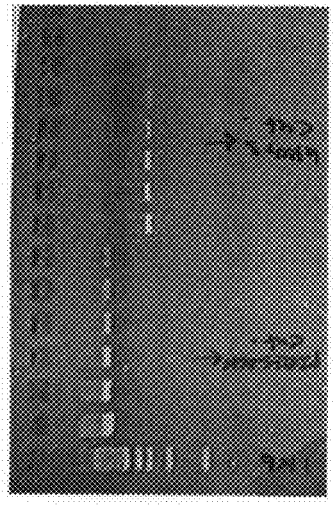

FIG. 2 is a photomicrograph serial dilutions of vector (pIRES2-EGFP) and insert (hKv1.3) before ligation. 1—1 Kb DNA Ladder (Biolabs cat#N3232S); 2—pIRES2-EGFP after digestion with restriction enzymes and purification; 3—hKv1.3 PCR amplification after digestion with restriction enzymes and purification.

Figure 3:
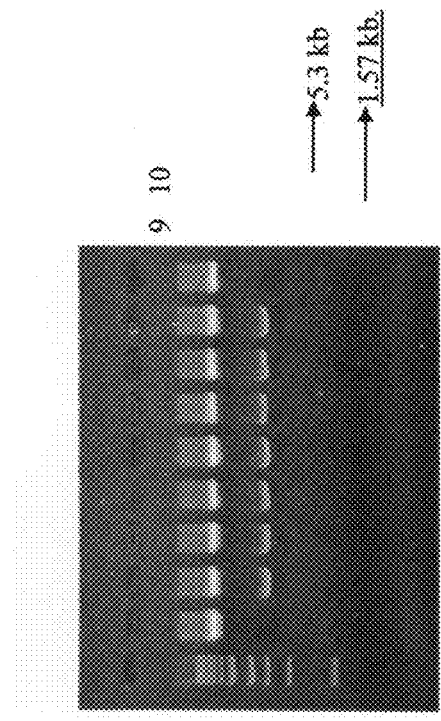

FIG. 3 is a photomicrograph showing DNA preparation from 8 transformed colonies following digestion with Bgl II and Sal I. Lane 1—1 kb DNA ladder; Lane 2—Negative control—pIRES2-EGFP; Lanes 3—10-colonies 1-8 minipreps.

Figure 4:
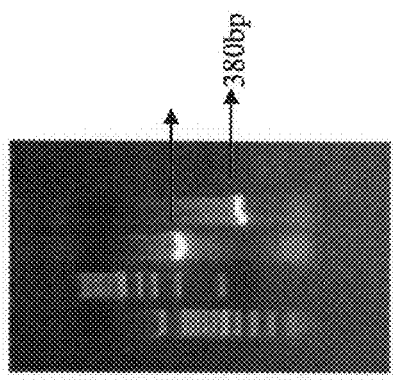

FIG. 4 is a photomicrograph showing two PCR fragments, Fragment A is 1200 by containing the wt sequence, Fragment B is 380 by containing the mutation sequence. Lane 1—100 bp DNA Ladder (Promega cat# G210A); Lane 2—1 kb DNA Ladder; Lane 3—amplification of Fragment A 1200 bp; Lane 4—amplification of fragment B 380 bp.

Figure 5:
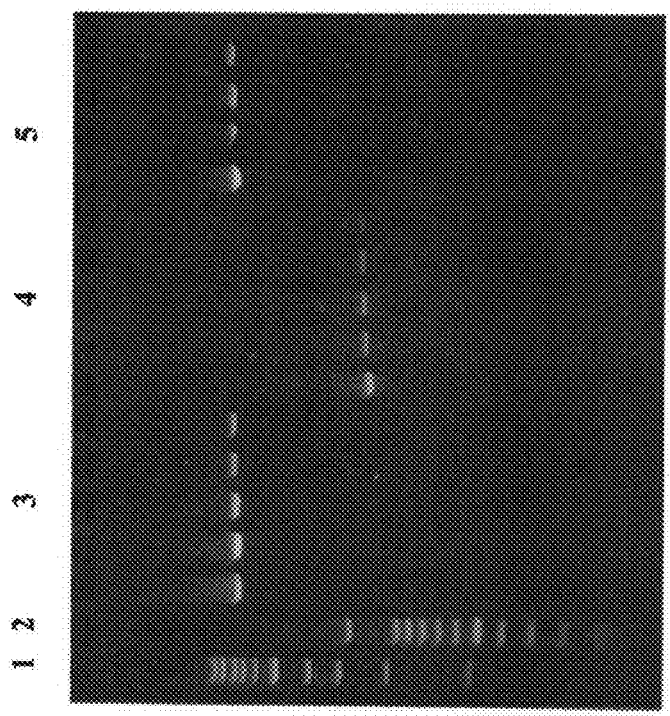

FIG. 5 is a photomicrograph showing serial dilutions of the vector and the two inserts (containing the mutation) prior to ligation. Lane 1—100 by DNA Ladder; Lane 2—1 kb DNA Ladder; Lane 3—pIRES2-EGF (digested with Bgl II and Sal I); Lane 4—Amplification B 380 by fragment (digested with EcoRI and Sal I); Lane 5—Amplification A 1200 by fragment (digested with Bgl II and Eco RI)

Figure 6:
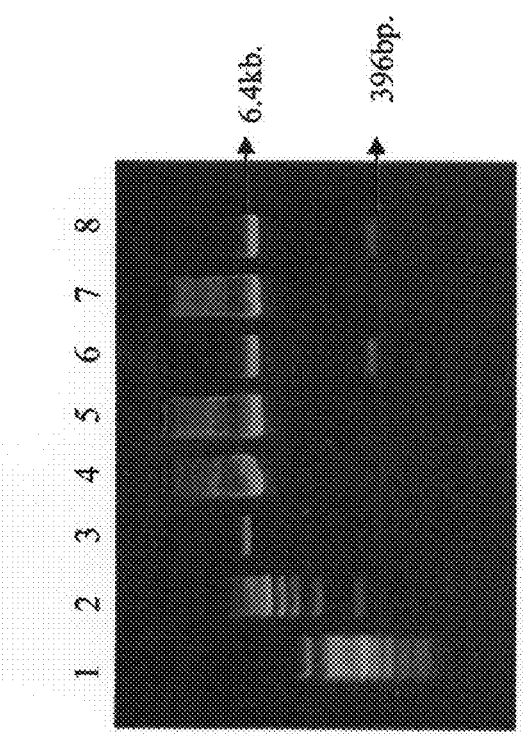

FIG. 6 is a photomicrograph showing that all clones (but clone number 1) are positive for the mutant insert. Lane 1—100 bp. DNA Ladder; Lane 2—1 Kb. DNA Ladder; Lane 3—clone #1 uncut; Lane 4—clone #1 cut; Lane 5—clone #2 uncut; Lane 6—clone #2 cut; Lane 7—clone #3 uncut; Lane 8—clone # 3 cut.

Figure 7:
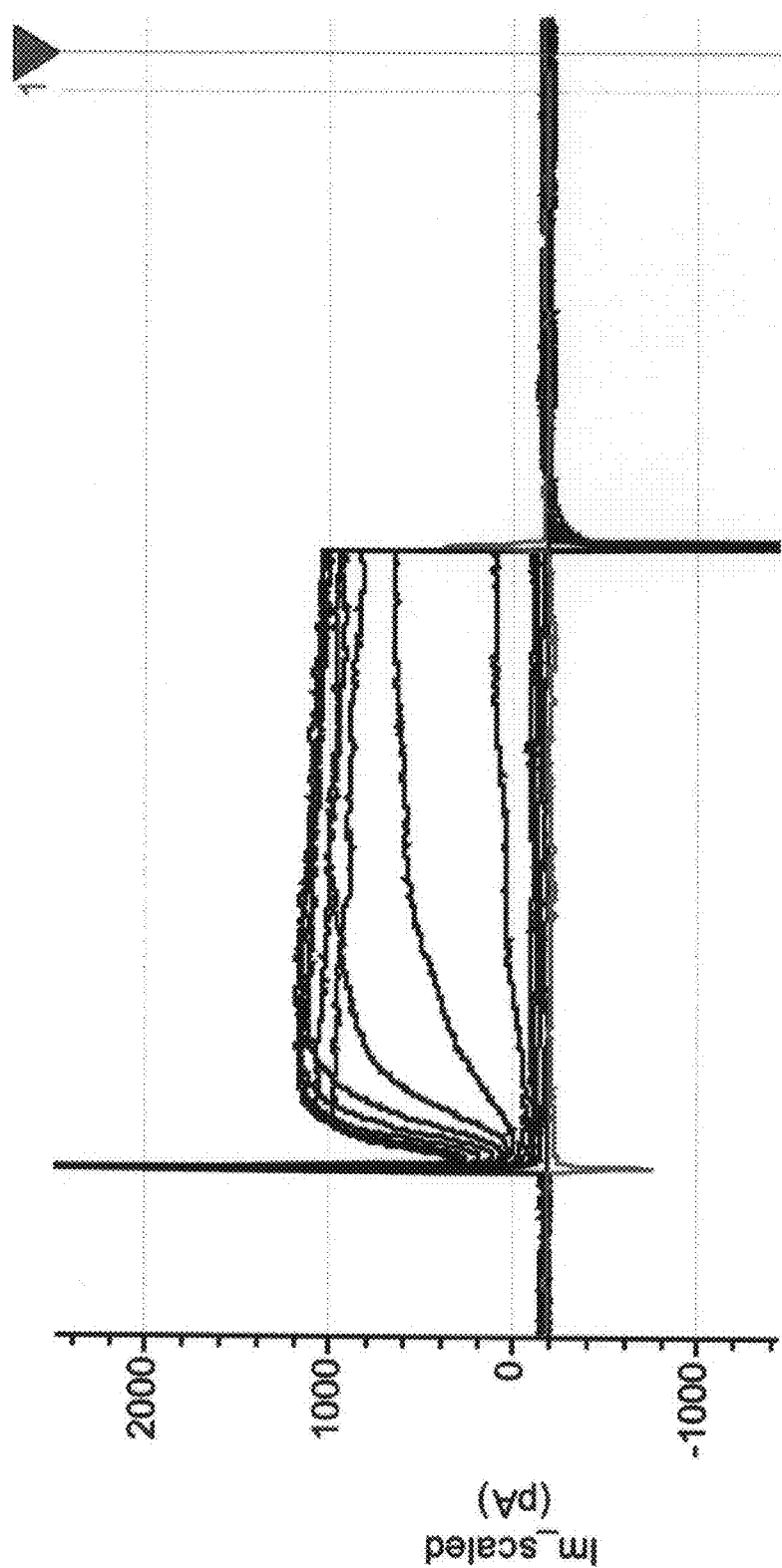

FIG. 7 is a patch clamp analysis showing potassium current from wild type hKv1.3 expressing NIH 3T3 cells.

Figure 8:
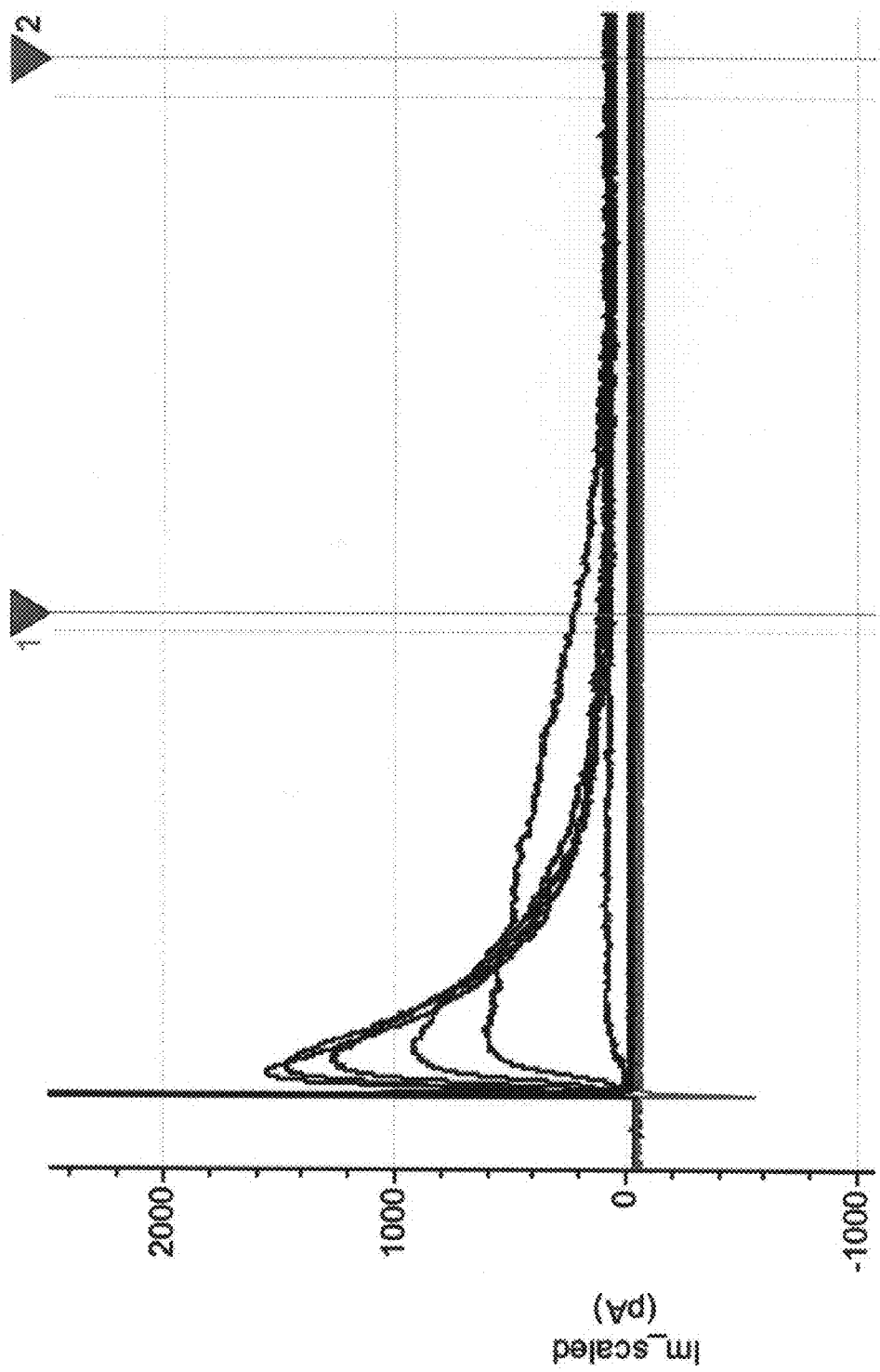

FIG. 8 is a patch clamp analysis showing potassium current from H399W hKv1.3 expressing NIH 3T3 cells.

Figure 9:
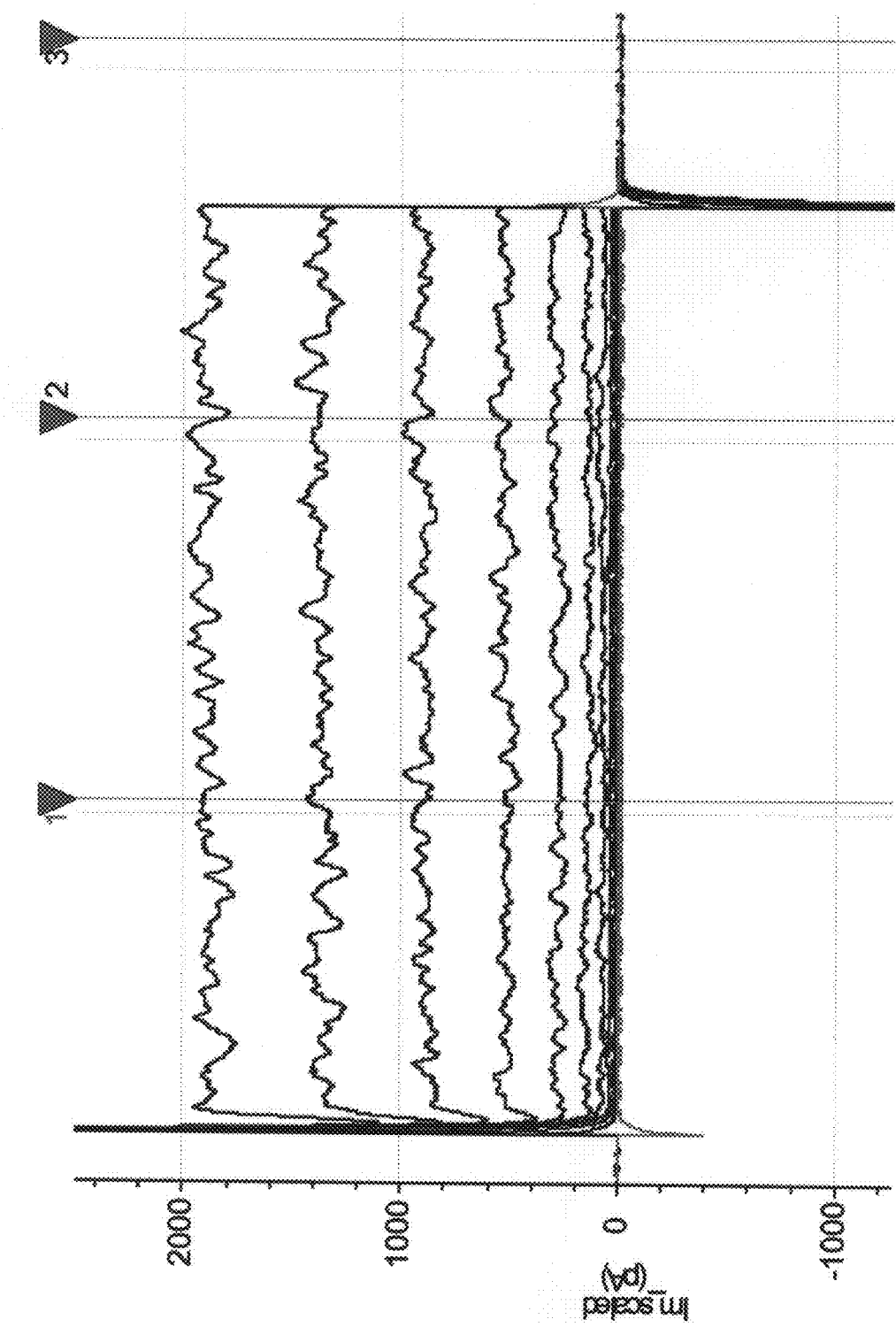

FIG. 9 is a patch clamp analysis showing potassium current from wild type hKv1.3 expressing human dermal fibroblasts.

Figure 10:
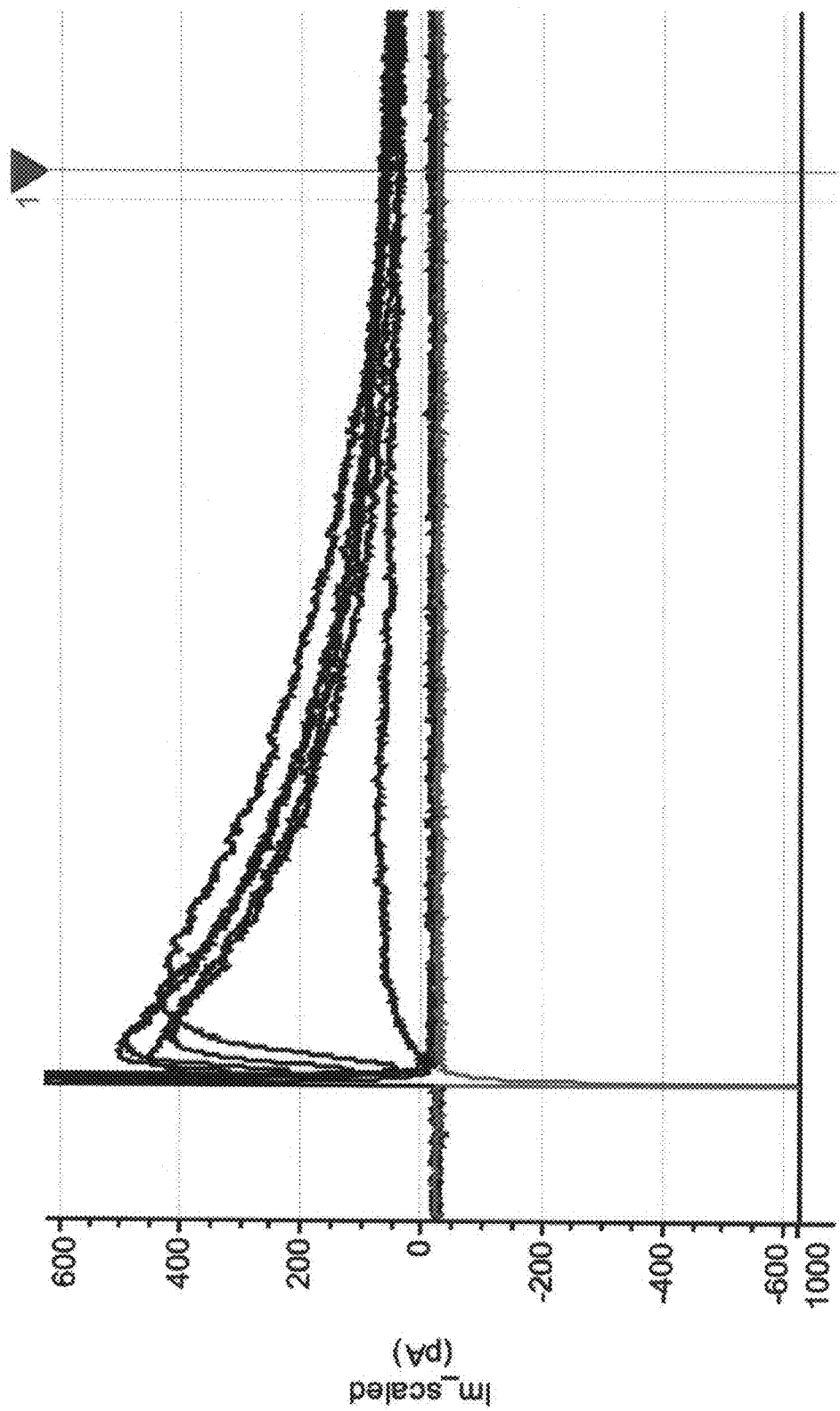

FIG. 10 is a patch clamp analysis showing potassium current from H399W hKv1.3 expressing human dermal fibroblasts.

DESCRIPTION OF THE PREFERRED EMBODIMENTS

The present invention is of novel hKv1.3 polynucleotide and polypeptide sequences which can be used in therapy and drug screening.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice the present inventors have genetically engineered a human Kv1.3 (hKv1.3) channel (GenBank Accession No. AAC31761, KCNA3) mutated to express tryptophan at position 399 instead of histidine. This mutation decreases the channel's recovery rate and as such can be used to treat a myriad of medical conditions linked to ion channel insufficiencies or dysfunctions (caused by or resultant from the pathology), especially, cardiac and neurological conditions in which prolongation of the refractory period is desired.

Thus, according to one aspect of the present invention there is provided a an isolated polynucleotide encoding a polypeptide comprising, contiguously, a first amino acid sequence being at least about 70%, at least about 80%, at least about 85%, at least about 90%, at least about 95% homologous to amino acid coordinates 1-398 of SEQ ID NO: 2, a tryptophan residue and a second amino acid sequence being at least about 70%, at least about 80%, at least about 85%, at least about 90%, at least about 95% homologous to amino acid coordinates 400-523 of SEQ ID NO:2.

Homology (e.g., percent homology) can be determined using any homology comparison software, including for example, the BlastP software of the National Center of Biotechnology Information (NCBI) such as by using default parameters.

Identity (e.g., percent homology) can be determined using any homology comparison software, including for example, the BlastN software of the National Center of Biotechnology Information (NCBI) such as by using default parameters.

As used herein the phrase "an isolated polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The polypeptide of this aspect of the present invention comprises a voltage-gated potassium channel activity.

As used herein the phrase "voltage-gated potassium channel activity" refers to opening and closing of the channel according to membrane potential. Methods of measuring voltage-gated potassium channel activity are known in the art. An exemplary method is further described in the Examples section hereinbelow (e.g., patch clamp).

According to a preferred embodiment of this aspect of the present invention an inactivation rate of the potassium channel is faster than that of a similar polypeptide having a histidine or a threonine residue instead of said tryptophan e.g., wild type Kv1.3 (SEQ ID NOs: 3 and 4).

The term "faster" as used herein is meant to encompass any increase in inactivation rate of the encoded polypeptide of this aspect of the present invention relative to the wild type protein for example (hKv1.3) e.g., the transition rate from open to inactivation of the wild type is 0.0074 (Marom. s. Toib. A. Braun. E. Rich dynamics in a simplified excitable system. Molecular and subcellular cardiology: effects of structure and function. 1995. 61:66.), Vs 0.025 for the H399W.

According to another preferred embodiment of this aspect of the present invention, inactivation of the channel is characterized by longer "tail current" than that of wild type hKv1.3, serving as a restraining current resisting an electrical activation, thereby increasing the refractory period of cells expressing same.

According to yet another preferred embodiment of this aspect of the present invention, the polynucleotide encodes a polypeptide having an amino acid sequence as set forth in SEQ ID NO: 2.

According to still another preferred embodiment of this aspect of the present invention the polynucleotide comprises a nucleic acid sequence as set forth in SEQ ID NO: 1.

The isolated polynucleotides of this aspect of the present invention can be qualified using a hybridization assay by incubating the isolated polynucleotides described above in the presence of oligonucleotide probe or primer under moderate to stringent hybridization conditions.

As used herein the term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

Oligonucleotides designed according to the teachings of the present invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example:

Sambrook, J. and Russell, D. W. (2001), "Molecular Cloning: A Laboratory Manual"; Ausubel, R. M. et al., eds. (1994, 1989), "Current Protocols in Molecular Biology," Volumes John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the present invention is of at least 17, at least 18, at least 19, at least 20, at least 22, at least 25, at least 30 or at least 40, bases specifically hybridizable with polynucleotide sequences of the present invention.

Moderate to stringent hybridization conditions are characterized by a hybridization solution such as containing 10% dextrane sulfate, 1 M NaCl, 1% SDS and $5 \times 10^6$ cpm $^{32}$P labeled probe, at 65° C., with a final wash solution of 0.2× SSC and 0.1% SDS and final wash at 65° C. and whereas moderate hybridization is effected using a hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

Preferably, an oligonucleotide of this aspect of the present invention is capable of specifically hybridizing to the above-described isolated polynucleotide (e.g., SEQ ID NO: 1) and not to a polynucleotide encoding a Kv1.3 polypeptide devoid of the tryptophan residue (e.g., wild type hKv1.3 SEQ ID NO: 3, GenBank Accession No. AAC31761).

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode a previously unidentified polypeptide, the present invention also encompasses novel polypeptides or portions thereof, which are encoded by the isolated polynucleotides and respective nucleic acid fragments thereof described hereinabove.

The present invention also encompasses polypeptides encoded by the polynucleotide sequences of the present invention.

The present invention also encompasses homologues of these polypeptides, such homologues can be at least about 70%, at least about 75%, at least about 80%, at least about 85%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO: 2.

The present invention also encompasses fragments of the above described polypeptides and polypeptides having mutations, such as deletions, insertions or substitutions of one or more amino acids, either naturally occurring or man induced, either randomly or in a targeted fashion.

Amino acid sequence information of the polypeptides of the present invention can be used to generate antibodies, which specifically bind to the polypeptides of the present invention.

Thus, according to yet another aspect of the present invention there is provided an antibody comprising an antigen recognition domain capable of specifically binding the polypeptide of the present invention (see above) and incapable of binding a human Kv1.3 polypeptide devoid of the tryptophan residue (SEQ ID NO: 2).

Such antibodies can be directed at a peptide sequence at least 4, at least 5, at least 8, at least 10 amino acids in length derived from the above described polypeptide sequences and comprising the tryptophan residue.

As used herein, the term "antibody" refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote RJ. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

After antibodies have been obtained, they may be tested for activity, for example via enzyme-linked immunosorbent assay (ELISA).

As mentioned hereinabove, the polynucleotides and polypeptides of the present invention can be used in numerous applications such as for altering cellular excitability and for screening of ion channel modulators, as will be further described hereinbelow.

To this end, the isolated polynucleotide of the present invention is preferably ligated into a nucleic acid construct suitable for cell (e.g., mammalian) expression. Such a nucleic acid construct includes a promoter sequence for directing transcription of the polynucleotide sequence in the cell in a constitutive or inducible manner.

Constitutive promoters suitable for use with the present invention are promoter sequences that are active under most environmental conditions and most types of cells, such as the cytomegalovirus (CMV) and Rous sarcoma virus (RSV). Inducible promoters suitable for use with the present invention include for example the tetracycline-inducible promoter (Zabala, M. et al. (2004). Optimization of the Tet-on system to regulate interleukin 12 expression in the liver for the treatment of hepatic tumors. Cancer Res 2004, 64(8), 2799-2804).

The nucleic acid construct (also referred to herein as an "expression vector") of the present invention includes additional sequences that render this vector suitable for replication and integration in prokaryotes, eukaryotes, or preferably both (e.g., shuttle vectors). In addition, a typical cloning vector may also contain transcription and translation initiation sequences, transcription and translation terminators, and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1.000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus or human or murine cytomegalovirus (CMV) and the long tandem repeats (LTRs) from various retroviruses, such as murine leukemia virus, murine or Rous sarcoma virus, and HIV. See Gluzman, Y. and Shenk, T., eds. (1983). Enhancers and Eukaryotic Gene Expression, Cold Spring Harbor Press, Cold Spring Harbor, N.Y., which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention may further comprise polynucleotide sequences that allow, for example, the translation of several proteins from a single mRNA, such as an internal ribosome entry site (IRES) and sequences for genomic integration of the promoter-chimeric polypeptide.

Examples for mammalian expression vectors include, but are not limited to, pcDNA3, pcDNA3.1 (+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Barr virus include pHEBO and p2O5. Other exemplary vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (AcMNPV), as described by Liang, C. Y. et al. (2004). High efficiency gene transfer into mammalian kidney cells using baculovirus vectors. Arch Virol 149, 51-60.

Recombinant viral vectors are useful for in vivo expression since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into stem cells. Such methods are generally described in, for instance: Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass.; and Gilboa, E. et al. (1986). Transfer and expression of cloned genes using retro-viral vectors. Biotechniques 4(6), 504-512; and include, for example, stable or transient transfection, lipofection, electroporation, and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Host cells of the present invention may be any cells useful for recombinant expression. For therapeutic applications the cells can be any suitable cells (syngeneic or allogeneic, human or non-human), such as, but not limited to, fibroblasts, neural cells, glial cells, stem cells, kidney cells, endothelial cells, cells of the cardiac tissue (e.g., cardiac stem cells, satellite cells, myoblasts, cardiomyocytes) bone marrow cells, keratinocytes, and lymphocyte cells (e.g., CTLs). Cells may be transfected in vitro, ex vivo or in vivo with the polynucleotides of the present invention.

As shown in Example 2 of the Examples section which follows, the polynucleotides of the present invention can be used to modify the excitability of cells transfected therewith.

This suggests that polynucleotides of the present invention and accordingly other mutants of hKv1.3 exhibiting an altered activation/inactivation rate compared to the wild type channel can be used to treat medical conditions associated with altered excitability. Examples of such channels include but are not limited to SEQ ID NOs. 1, 2, 5, 6, 7, 8, 9 and 10.

Thus according to an additional aspect of the present invention there is provided a method of treating a medical condition associated with ion channel insufficiency or dysfunction (as mentioned hereinabove, caused by or resultant from the pathology) or medical conditions which can be improved by overexpression of hKv1.3 polypeptides with an engineered activation/inactivation pattern.

As used herein the term "treating" refers to inhibiting or arresting the development of a disease, disorder or condition and/or causing the reduction, remission, or regression of a disease, disorder or condition in a subject suffering from, being predisposed to, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

Examples of diseases and conditions which can be treated using the constructs and/or cells of the present invention include, but are not limited to glucose regulation disorders (e.g., diabetes mellitus), cardiac arrythmia (e.g., bradycardia, atrial fibrillation) diseases which are treatable by modulating (i.e., increasing or decreasing) the refractory period of a cardiac tissue (e.g., atrial fibrillation, atrial flutter, atrial tachycardia and ventricular tachycardia), diseases which are treatable by modulating (i.e., increasing or decreasing) neural excitability (e.g., epilepsy, Parkinson's disease and Alzheimer's disease) and diseases and conditions which are treatable by modulating (i.e., increasing or decreasing) pyramidal or purkinje cell coupling (e.g., cerebrovascular accident, epilepsy and pain (e.g., phantom pain). Since the hKv1.3 also plays a role in the development of inflammatory conditions and autoimmune diseases, the latter are also included within the scope of the present invention [see e.g., Beeton et al. Proc Natl Acad Sci USA. 2006 Nov. 14; 103(46): 17414-9].

A preferred example contemplates the use of hKv1.3 mutants which prolong the refractory period (e.g., H399W and A413V or a combination of same; see e.g., Example 2 of the Examples section and Panyi et al. 1995 Biophysical J. 69: 896-903) for the treatment of diseases which can benefit from same (e.g., cardiac conditions such as atrial fibrillation, neurological conditions such as Parkinson's disease and epilepsy).

Another preferred example contemplates the use of hKv1.3 mutants which shorten the refractory period (e.g., H399T, A413C and a combination of same see e.g., Dreker and Grissmer 2005 Mol. Pharmacol. 68: 966-973) and increase tissue excitability for the treatment of diseases which can benefit from same (e.g., the treatment of Alzheimer's disease, and other neurodegenerative disorders). Table 1 below illustrates some ex-vivo embodiments of this aspect of the present invention in terms of the target indication, the preferred cells for use and the delivery site.

TABLE 1

| Tissue | Medical condition | Preferred cells | Preferred site of administration site |
|---|---|---|---|
| Cardiac | Generation of conduction block for the treatment of Ventricular tachycardia | Fibroblasts Mesenchymal stem cells Myoblasts Cardiomyocytes Endothelial cells | Infarct zone Around Infarct zone |

TABLE 1-continued

| Tissue | Medical condition | Preferred cells | Preferred site of administration site |
|---|---|---|---|
| | Generation of rate dependent conduction block for the treatment of Ventricular tachycardia | Fibroblasts Mesenchymal stem cells Myoblasts Cardiomyocytes Endothelial cells | Infarct zone Around Infarct zone |
| | AV node modification for the treatment of atrial fibrillation | Fibroblasts Mesenchymal stem cells Myoblasts Cardiomyocytes Endothelial cells | AV nodal area Bundle of His Slow pathway Fast pathway |
| | Rhythm control treatment of atrial fibrillation by generation of conduction block or rate dependent conduction block or by silencing areas with fractionated potentials or by isolating the pulmonary veins | Fibroblasts Mesenchymal stem cells Myoblasts Cardiomyocytes Endothelial cells | In the atria wall (Maze form) Area with fractionated potentials Around the pulmonary veins |
| | Ventricular tachycardia treatment by silencing ectopic foci or generation of conduction block in reentrant circle or by silencing scar tissue region. | Fibroblasts Mesenchymal stem cells Myoblasts Cardiomyocytes Endothelial cells | Ectopic foci At a reentrant circle Infarct zone Around an infarct |
| Neural | epilepsy by silencing ectopic foci | Fibroblasts Mesenchymal stem cells Myoblasts Cardiomyocytes Endothelial cells Glia cells | Ectopic foci |
| | Parkinson's disease by silencing specific locations in the basal ganglia | Fibroblasts Mesenchymal stem cells Myoblasts Cardiomyocytes Endothelial cells Glia cells | STN GPi SNr |
| | ALS by silencing specific locations in the basal ganglia | Fibroblasts Mesenchymal stem cells Myoblasts Cardiomyocytes Endothelial cells Glia cells | STN GPi SNr |

A specifically preferred treatment modality is described in PCT Application WO2006/018836 herein incorporated by reference.

The constructs according to the present invention can be administered to the subject (i.e., mammalian e.g., human) per se, or in a pharmaceutical composition where it is mixed with suitable carriers or excipients.

Thus, according to another preferred embodiment of the present invention, the nucleic acid constructs according to the teachings of the present invention are included in a pharmaceutical composition which also includes a pharmaceutically acceptable carrier which serves for stabilizing and/or enhancing the accessibility or targeting of the constructs to target tissues.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect, i.e. the nucleic acid constructs of the present invention.

Hereinafter, the phrases "physiologically acceptable carrier" and "pharmaceutically acceptable carrier" are interchangeably used to refer to a carrier, such as, for example, a liposome, a virus, a micelle, or a protein, or a dilutent which do not cause significant irritation to an organism and do not abrogate the biological activity and properties of the active ingredient. An adjuvant is included under these phrases.

Herein the term "excipient" refers to an inert substance added to a pharmaceutical composition to further facilitate administration of an active ingredient. Examples, without limitation, of excipients, include calcium carbonate, calcium phosphate, various sugars and types of starch, cellulose derivatives, gelatin, vegetable oils and polyethylene glycols.

Techniques for formulation and administration of compositions may be found in "Remington's Pharmaceutical Sciences," Mack Publishing Co., Easton, Pa., latest edition, which is incorporated herein by reference.

Suitable routes of administration are preferably local rather than systemic, for example, via injection of the preparation directly into the excitable tissue region. For injection, the active ingredients of the invention may be formulated in aqueous solutions, preferably in physiologically compatible buffers such as Hank's solution, Ringer's solution, or physiological salt buffer.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically.

Pharmaceutical compositions suitable for use in context of the present invention include compositions wherein the active ingredients are contained in an amount effective to achieve the intended purpose.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer of the active ingredient. Such information can be used to more accurately determine useful doses in humans.

Toxicity and therapeutic efficacy of the active ingredients described herein can be determined by standard pharmaceutical procedures in vitro, in cell cultures or experimental animals (i.e., animal models). The data obtained from these in vitro and cell culture assays and animal studies can be used in formulating a range of dosage for use in human. The dosage may vary depending upon the dosage form employed. (See e.g., Fingl, et al., 1975, in "The Pharmacological Basis of Therapeutics", Ch. 1 p. 1).

Animal models suitable for use in accordance with the present invention are well known in the art. For example, acute atrial fibrillation can be induced pigs by burst atrial pacing [Donahue J K, Heldman A. W, Fraser H, McDonald A D, Miller J M, Rade J J, Eschenhagen T, Marban E. Focal modification of electrical conduction in the heart by viral gene transfer. Nat Med. 2000 Dec.; 6(12):1395-8]. 6-OHDA-lesioned mice may be used as animal models of Parkinson's. In addition, a sunflower test may be used to test improvement in delicate motor function by challenging the animals to open sunflowers seeds during a particular time period. Transgenic mice may be used as a model for Huntingdon's disease which comprise increased numbers of CAG repeats have intranuclear inclusions of huntingtin and ubiquitin in neurons of the striatum and cerebral cortex but not in the brain stem, thalamus, or spinal cord, matching closely the sites of neuronal cell loss in the disease.

Transgenic mice may be used as a model for ALS disease which comprise SOD-1 mutations.

The septohippocampal pathway, transected unilaterally by cutting the fimbria, mimics the cholinergic deficit of the septohippocampal pathway loss in Alzheimers disease. Accordingly animal models comprising this lesion may be used to test the cells of the present invention for treating Alzheimers.

Survival and rotational behavior (e.g. on a rotarod) of the animals may be analyzed following administration of the cells of the present invention. For diabetes: alloxan and STZ-treated mice; 90%-pancreatectomized rats Direct administration of the nucleic acid constructs described hereinabove or of pharmaceutical compositions including such constructs into cells forming a part of, or being in contact with, the excitable tissue region is preferably used in cases where the cells of the excitable tissue to be transformed are viable and functional.

In cases where cell damage or death defines a disorder of excitable tissue, the preferred mode of treatment is implantation of transformed or non-transformed cells having ion channels/transporters and gap junctions.

Thus, according to another aspect of the present invention there is provided a method of modifying the electrophysiological function of an excitable tissue region of an individual. The method is effected by implanting cells into the excitable tissue region, wherein the implanted cells are each characterized by the ability to form gap junctions with at least one cell of the excitable tissue region and by the ability to form functional ion channels or transporters of one or more channel or transporter types.

Implantation of such cells can be effected by, for example, a syringe and needle adapted or fabricated for cell implantation, by a catheter drug delivery system (see for example, U.S. Pat. No. 6,102,887) or by standard neurosurgical methods.

As mentioned above, the implanted cells can be cells expressing endogenous ion channel and/or gap junction polypeptides, or modified cells transformed with the nucleic acid constructs of the present invention. Preferably, the implanted cells are mammalian cells, such as for example, muscle, or fibers cells (see the Examples section for further detail).

Administration of the cells of the present invention can be effected using any suitable route of introduction, such as intravenous, intraperitoneal, intra-kidney, intra-gastrointestinal track, subcutaneous, transcutaneous, intramuscular, intracutaneous, intrathecal, epidural, and rectal. According to presently preferred embodiments, the cells of the present invention may be introduced to the individual using intravenous, intra-kidney, intra-gastrointestinal track, and/or intraperitoneal administration.

Cells of the present invention can be derived from either autologous sources, such as self bone marrow cells, or from allogeneic sources, such as bone marrow or other cells derived from non-autologous sources. Since non-autologous cells are likely to induce an immune reaction when administered to the body, several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxy-cinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 µm. Such microcapsules can be further encapsulated with an additional 2-5 µm of ter-polymer shells in order to impart a negatively charged smooth surface and to minimize plasma protein absorption (Chia, S. M. et al. (2002). Multilayered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 µm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

The newly engineered potassium channels of the present invention may be used to identify agents which affect voltage gated potassium channel activity (either intentionally or as a side effect). This may be effected by determining an activity of the Kv1.3 polypeptide the present invention in the presence and absence of the agent, wherein a change in the activity of the Kv1.3 polypeptide is indicative of an agent capable of affecting/regulating the activity of the voltage-gated potassium channel.

Agents (e.g., small-molecules, peptides, analogs, mimetics) that affect/regulate the biological activity of the voltage-gated potassium channel subunit described herein are contemplated for use in the treatment of a wide variety of medical conditions.

Thus the present invention provides novel channel compositions and methods of using same for the treatment of medical conditions associated with insufficient or altered tissue excitability and for the identification of agents capable of regulating the activity of voltage-gated potassium channels.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Cloning of the Human Kv1.3 Ion Channel

In order to create Kv1.3 ion channel with prolonged tail current, the human Kv1.3 channel was cloned and the amino acid residue Histidine (H) at position 399, was replaced by the amino acid Tryptophan (W), using PCR-assisted mutagenesis.

pSP64 cloning vector which comprises the human Kv1.3 was used as a PCR template to amplify the hKV1.3 (1571 bp.) cDNA using primers with designed restriction sites. The 1571 bp fragment was cloned into pIRES2-EGFP (BD Biosciences Clontech Catalog No. 632306) mammalian expression vector. The H399W mutation was introduced by another PCR with 2 pairs of primers containing the mutated sequence in 2 fragments 340 bp and 1231 bp. The fragments were extracted from the gel and ligated into pIRES2-EGFP cloning vector. The wild type fragment was then exchanged with the mutated fragment using 3 fragment ligation. Positive colonies were sequenced, and the mutation was expressed in cells.

Cloning of wild type (wt)Kv1.3 in pIRES2-EGFP—Kv1.3 (1571 bp.) gene was amplified by polymerase chain reaction (PCR) using pS64-KV1.3 as a template for amplification. The following primers were used:

```
Forward primer A:
                                       (SEQ ID NO: 11)
GAAGATCTATGACCGTGGTGCCC containing BglII restriction site;
and Reverse primer 1B:
                                       (SEQ ID NO: 12)
CCGGTCGACTTAAACATCGGTGAA containing SalI restriction site.
```

PCR amplification reaction for Kv1.3 wt gene was performed in 50 µl volume using 50 ng of pDNA template, 50 pmol of each primer, 200 µM of each dNTP (Promega Catalog No. E6000), 1×Pfu DNA Polymerase buffer, and 1.0 U of Pfu DNA Polymerase (Promega Catalog No. M7741). The reaction mixture was subjected to a 95° C. denaturation for 2 minutes, followed by 35 cycles of: 95° C. 1 minute; 55° C. 30 seconds and 72° C. 4 minutes. The reaction was effected using Biometra thermal cycler. PCR amplification was analyzed by 1 agarose gel with GelStar nucleic acid gel stain (BMA Catalog No. 50535) see FIG. 1. The PCR fragment and pIRES2-EGFP were digested by Bgl II (Roch Applied Science Catalog No. 10 567 639 001) and Sal I (Roch Applied Science Catalog No. 10 567 663 001), and isolated from 0.7% agarose gel using gel extraction kit (Qiagen®; Cat. No: 28704) see FIG. 2. After isolating the digesting fragments from the gel, the digested vector and insert were put together in an Eppendorff tube with a molar ratio of vector and insert of 1:3 (vector:insert) and ligated using T4 DNA Ligase (Roch Applied Science cat #481220). The ligation was performed in a 30 µl volume, overnight at 4° C. 7 µl of the ligation mixture were transformed to JM109 competent cells (Promega cat #L2001) using the protocol suggested by the manufacturer.

The transformed cells were plated on LB with 30 μg/ml Kanamycine Sulfate (Sigma Catalog No. 60615-5G) for selection and incubated for overnight at 37° C. Eight colonies were picked and inoculate into 3 ml LB with 30 μg/ml Kanamycine overnight, then plasmids were isolated from each colony culture by Wizard Plus Miniprep DNA Purification System (Promega cat #A7100) according to the protocol suggested by the manufacturer. 1 μg from every sample were digested with Bgl II and Sal I to test if colonies contain the insert (Kv1.3). As can be seen from FIG. 3, 7 colonies were found to positively contain the 1.57 kb insert fragment.

Sequencing of the Kv1.3 wt gene—Constructs from colonies 1-3 were sequenced using dye-terminator cycle sequencing with an ABI 3700 to verify incorporation of the intended insert and to confirm that no unwanted changes were introduced. The sequencing was performed at the Center of Genomic Technologies at the Hebrew University.

The sequence of clone # 1 (SEQ ID NO: 17) is similar to the sequence of human potassium channel Kv1.3 in gene bank (GI:25952081), no unwanted changes were found in this sequence. This clone was used as a PCR template to produce the H399W mutation.

H399W mutagenesis—Two PCR amplifications were performed in 50 μL volume each.
1. Amplification A: 1200 bp fragment:
Primers:

```
Forward primer 1A:
GAAGATCTATGACCGTGGTGCCC containing Bgl II restriction site
(restriction site is highlighted, SEQ ID NO: 13)

Reverse primer 2A:
CCGGAATTCCCCACTGTTGTCAT containing Eco RI restriction site
(restriction site is highlighted, SEQ ID NO: 14)
```

2. Amplification B: 400 bp fragment containing the mutation:
Primers:

```
Forward primer 2B (SEQ ID NO: 15):
CCGGAATTCTTACGGCGATATGTGGCCAGTGAC
```

This primer is containing the mutant sequence TGG (bolded) instead of CAC and Eco RI restriction site (restriction site is highlighted)

```
Reverse primer 1B (SEQ ID NO: 16):
CCGGTCGACTTAAACATCGGTGAA containing Sal I restriction site
(restriction site is highlighted).
```

In each amplification 50 pmol of each primer, 50 ng of pIRES2-EGFP-Kv1.3 (clone #1), 200 μM of each dNTP (Promega Catalog No. E6000), 1×Pfu DNA Polymerase buffer, and 1.0 U of Pfu DNA Polymerase (Promega Catalog No. M7741) were used. The reaction mixture was subjected to a 95° C. initial denaturation for 2 min, followed by 35 cycles of 95° C. for 1 min 55° C. for 30 s, and 72° C. for 4 min using Biometra thermal cycler.

PCR fragments were analyzed by 1 Agarose gel with Gel-Star staining (FIG. 4). PCR products were purified with QIAquick PCR Purification Kit (QIAGEN Catalog No. 28104). Fragment A 1200 bp was digested with Bgl II (Roch Applied Science Catalog No. 10 567 639 001) and Eco RI (Roch Applied Science Catalog No. 10 703 737 001). Fragment B [containing the mutation was digested with EcRI and Sal I (Roch Applied Science Catalog No. 10 567 663 001)]. The vector (pIRES2-EGFP) was digested with Bgl II and Sal I.

All digested fragments were loaded onto 0.07% agarose gel and extracted by QIAquick Gel Extraction Kit (QIAGEN Catalog No. 28704) using the protocol suggested by the manufacturer. Gel extracts were analysed by 1% Agarose gel (FIG. 5):

Ligation was performed for the 3 fragments after isolation from the gel in 1:3:3 molar ratio vector: insertA:insertB using T4 DNA Ligase (Roch Applied Science cat #481220) in 30 μl reaction volume and incubated at 4° C. overnight. 7 μl of the ligation reaction were transformed into *E. COLI* JM109 Competent cells (Promega Catalog No. L2001). The cells were plated on LB with 30 μg Kanamycine for selection and incubated at 37° C. overnight. 3 Colonies were picked and inoculate into 3 ml LB kanamycine each and incubated with 225 rpm agitation at 37° C. overnight. Plasmids were isolated from each 3 ml colony culture by Wizard Plus Miniprep DNA Purification System (Promega cat #A7100) according to the protocol suggested by the manufacturer. 1 μg from each colony was digested with Sal I and EcoRI to check if the clone was positive. FIG. 6 shows positive clones generating 2 bands upon restriction. First band: fragment A (396 bp). Second band: pIRES2-EGFP+ fragment B (6.4 kb). 100 ng from each reaction were loaded onto 1% agarose gel for analysis (FIG. 6).

Constructs from colonies 2 and 3 were sequenced using dye-terminator cycle sequencing with an ABI 3700 to verify incorporation of the intended amino acid change and to confirm that no unwanted changes unless the mutation were introduced. The sequencing was performed at the Center of Genomic Technologies at the Hebrew University. SEQ ID NOs. 17 and 18 show that the mutation was generated, without unwanted changes at the amino acid sequence.

Large scale preparation of the mutated construct produced 1 mg DNA which was stored at 4° C. (Promega Wizard Plus Miniprep DNA Purification System cat #A7100).

Example 2

Expression of hKv1.3H399W in Eukaryotic cells

Two types of cells were used to express the H399W mutation:

Mouse fibroblasts cell line (NIH/3T3, ATCC ACCESSION NO. CRL-6361):

These cells do not express any type of potassium currents, and as such are suitable for testing potassium currents following transfection with different constructs (as Kv1.3 wt and Kv1.3H399W).

Human dermal fibroblasts: Although some of these cells exhibit endogenous potassium currents, this background current does not disturb the recordings of the current resulting from the overexpression of Kv 1.3.

Voltage clamp assay was used to test the expression and function of the over-expressed channels.

Materials and Experimental Procedures

Expression in NIH/3T3 cell line—NIH/3T3 cells were stably transfected using Lipofectin reagent (Invitrogen Catalog No. 182992) according to the protocol suggested by the manufacturer. Selection was done using Neomycin sulfate (G418) antibiotic (Gibco Catalog No. 11811-031) which was added to the growth medium (500 ng/ml). Clones were isolated using cloning ring and cultured into 24 well plate (corning Catalog No. 3524). For expansion, confluent wells were transferred to six well plates and then to 100 mm culture dish (Corning Catalog No. 430167DMEM-complete+G418 10% FCS was thereafter replaced every 72 to 96 hours.

Total cell protein was extracted from the various clones using 300 μl cold RIPA buffer (with supplements; RIPA lysis buffer, 1× Santa Cruz Biotechnology, Catalog No. 24948) and screened by western blot analysis with rabbit anti-Kv1.3 antibody (CHEMICON, Catalog No. AB5178). Colonies that tested western blot positive were then analyzed by voltage clamp.

Expression in Human Dermal Fibroblasts—HDF Cells were isolated from human skin using enzymatic extraction method according to the protocol suggested by Wang H et al (2004) In Vitro Cell Dev Biol Anim. The protocol is using Collagenase type 1 (Worthington Biochemical Corp., Lakewood, N.J., cat. LS004196, lot.X4J7447) for extractions of cells from a tissue. Primary cultures were generated by seeding in flasks with growth Medium: DMEM+HEPES (ADCF) with phenol red (HyClone part no SH3A1534.01, Lot no ANM20173 custom made for biogenics, L.T.D). Medium was supplemented with 10% FBS defined (HyClone; Cat no: SH30072.03; Lot no: APD21173); ITS+1 liquid media supplement (sigma # I-2521); Gentamycin 50 μg ml (Beit ha'emek; cat no#03-035-1) and Amphotericin B 2.5 μg ml (Beit ha'emek; Catalog No. 03-029-1).

Five days prior to transfection, cells were seeded in 150 cm² flasks. Medium was changed every 3 days. Cells reached 90% confluence in the day of the transfection.

For expression of the wt and mutation constructs in human dermal fibroblasts, Amaxa Nucleofector (Amaxa biosystem) and Human Dermal Fibroblast (NHDF) Nucleofector kit (Catalog No. VPD-1001) were used. Nucleofection was done according to the protocol of the manufacturer. Cells from passage 1-5 were used. The expression was characterized using fluorescent microscopy and the patch clamp technique. Seven days after nucleofection patch clamp analysis were performed.

Patch clamp recordings—Voltage-clamp recordings were performed using the whole-cell patch clamp technique. All measurements were done at room temperature. Patch pipettes (2-4 MΩ) were prepared from glass capillary tubes (Jencons Catalog No. 687-055) using a double-stage puller (Narishige pp-830). Currents were recorded with an Axon Instruments amplifier (Axopatch 200), digitized by DigiData 1322A digitizer (Axon instruments). Data was analyzed using pCLAMP software (version 8.0). Bath solution for the whole-cell recordings contained (in mM): 140 NaCl, 3 KCl, 2 $CaCl_2$, 2 $MgCl_2$, 10 Glucose and 10 HEPES (pH 7.4). Pipette solution for the whole-cell recordings (in mM): 140 KCl, 10 $Na_2$ ATP, 1 $CaCl_2$, 1 $MgCl_2$, 10 EGTA and 5 HEPES (pH 7.4). Currents were elicited by 200 ms pulses from holding potential of −80 mV to −90 mv and then to 110 mV in increments of 20 mV. Kv1.3:H401W currents are characterized by fast inactivation kinetic in compare to the wild type Kv1.3 currents.

Results

NIH/3T3 patch clamp—Patch clamp recordings were performed on two different clones of every construct (wt Kv1.3 and mutant). FIG. 7 shows the slowly inactivated wild type Kv1.3 potassium current measured from NIH/3T3 fibroblasts cell line transfected with the wild type channel. Similar currents (amplitude 200-1500 pA) were measured from more cells that were transfected with this plasmid.

FIG. 8 shows the fast inactivated potassium current from NIH/3T3 fibroblasts cell line that was transfected with pIRES2-EGFP-H399W. Similar currents (amplitude 150-1800 pA) were measured from all the cells that were transfected with this plasmid.

Human Dermal fibroblasts patch clamp—Currents were measured from 24 cells: 12 transfected with wt hKv1.3 and 12 transfected with hKv1.3H399W. Recordings were done 7-20 days after nucleoporation. Recorded cells were from different passages (3-6). All recorded cells were positive. All of the transfected cells presented potassium current (with variable amplitude 400-2500 pA). All of the wt kv1.3 transfected cells presented typical potassium (amplitude 600-2500 pA) current FIG. 9. All of the H399W transfected cells presented fast inactivated potassium current (amplitude 400-1200 pA, FIG. 10).

Thus, the Human Kv1.3H399W generates fast inactivation properties which render it suitable for therapy in terms of immunogenicity being of human origin and biophysical properties of fast inactivation and therefore expressing long tail currents.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated polynucleotide comprising a nucleic acid sequence encoding the polypeptide having the amino acid sequence as set forth in SEQ ID NO: 2.

* * * * *